(12) United States Patent
Schaubroeck et al.

(10) Patent No.: US 8,927,670 B2
(45) Date of Patent: Jan. 6, 2015

(54) MULTICOORDINATED METAL COMPLEXES FOR USE IN METATHESIS REACTIONS

(75) Inventors: David Schaubroeck, Roeselare (BE); Stijn Monsaert, Zottegem (BE); Nele Ledoux, Poperinge (BE); Francis Verpoort, Gits (BE); Renata Drozdzak, Roubaix (FR)

(73) Assignee: RIMTEC Corporation, Tokyo (JP)

( * ) Notice: Subject to any disclaimer, the term of this patent is extended or adjusted under 35 U.S.C. 154(b) by 782 days.

(21) Appl. No.: 11/465,651

(22) Filed: Aug. 18, 2006

(65) Prior Publication Data

US 2007/0043188 A1 Feb. 22, 2007
US 2008/0293905 A9 Nov. 27, 2008

Related U.S. Application Data

(60) Provisional application No. 60/710,073, filed on Aug. 22, 2005.

(30) Foreign Application Priority Data

Aug. 22, 2005 (GB) .................................. 0517137.6

(51) Int. Cl.
| | | |
|---|---|---|
| C08F 136/00 | (2006.01) | |
| B01J 31/00 | (2006.01) | |
| B01J 31/22 | (2006.01) | |
| C07F 15/00 | (2006.01) | |
| C07F 17/02 | (2006.01) | |
| C08G 61/06 | (2006.01) | |
| C08G 61/08 | (2006.01) | |

(52) U.S. Cl.
CPC .......... *B01J 31/2278* (2013.01); *B01J 31/2273* (2013.01); *C07F 15/0046* (2013.01); *C07F 17/02* (2013.01); *C08G 61/06* (2013.01); *C08G 61/08* (2013.01); *B01J 2231/54* (2013.01); *B01J 2531/821* (2013.01)
USPC ........................................... 526/283; 502/150

(58) Field of Classification Search
USPC ........................................................ 556/30
See application file for complete search history.

(56) References Cited

U.S. PATENT DOCUMENTS

| 5,763,548 A | 6/1998 | Matyjaszewski et al. |
| 5,977,393 A * | 11/1999 | Grubbs et al. .................. 556/21 |
| 6,284,852 B1 | 9/2001 | Lynn et al. |

(Continued)

FOREIGN PATENT DOCUMENTS

| EP | 0563730 A2 | 10/2003 |
| EP | 1577282 A3 | 11/2005 |

(Continued)

OTHER PUBLICATIONS

Trnka et al., Acc. Chem. Res. 2001, 34, 18-29.*

(Continued)

*Primary Examiner* — Yun Qian
(74) *Attorney, Agent, or Firm* — Clark & Elbing LLP

(57) ABSTRACT

Improved catalysts useful in alkyne or olefin metathesis are made by bringing into contact a multi-coordinated metal complex comprising a multidentate Schiff base ligand, and one or more other ligands, with a selected activating compound under conditions such that at least partial cleavage of a bond between the metal and the multidentate Schiff base ligand of said metal complex occurs.

18 Claims, 5 Drawing Sheets

(56) References Cited

U.S. PATENT DOCUMENTS

| | | | |
|---|---|---|---|
| 6,407,187 | B1 | 6/2002 | Matyjaszewski et al. |
| 6,512,060 | B1 | 1/2003 | Matyjaszewski et al. |
| 6,541,580 | B1 | 4/2003 | Matyjaszewski et al. |
| 6,576,779 | B1 | 6/2003 | Bansleben et al. |
| 6,624,263 | B2 | 9/2003 | Matyjaszewski et al. |
| 6,696,597 | B2 | 2/2004 | Pederson et al. |
| 2002/0193538 | A1 | 12/2002 | Matyjaszewski et al. |
| 2005/0043541 | A1 | 2/2005 | Walter et al. |
| 2007/0185343 | A1* | 8/2007 | Verpoort et al. ............ 556/30 |
| 2008/0227851 | A1* | 9/2008 | Wender ..................... 514/450 |

FOREIGN PATENT DOCUMENTS

| | | |
|---|---|---|
| WO | WO 99/22856 | 5/1999 |
| WO | WO 03/062253 A1 | 7/2003 |
| WO | WO 2005/035121 A2 | 4/2005 |
| WO | WO 2005/035121 A3 | 4/2005 |

OTHER PUBLICATIONS

Opstal et al. Angew. Chem. Int. Ed. 2003, 42, 2876-2879.*
Drozdzak et al. (Central European Science Journal, 2005, 404-416.*
Sanford et al. Organometallics, 1998, 17, 5384-5389.*
Biradar et al., "Trinuclear Complexes of Dimethylsilane and Cobalt Schiff-Base Complexes," *Inorganics Chimica Acta*, 74:39-41 (1983).
Opstal et al., "Easily Accessible Ring Opening Metathesis and Atom Transfer Radical Polymerization Catalysts based on Arene, Norbornadiene and Cyclooctadiene Ruthenium Complexes Bearing Schiff Base Ligands," *Adv. Synth. Catal.* 345: 393-401 (2003).
Trnka et al., "The Development of $L_2X_2Ru$=CHR Olefin Metathesis Catalysts: An Organometallic Success Story," *Acc. Chem. Res.* 34:18-29 (2001).
EPO search report (EP Application Serial No. 06017332.5—Patent No. 2117) mailed Nov. 28, 2006.
International Search Report for PCT/EP2006/008221, mailed Mar. 2, 2007.
Written Opinion of the International Searching Authority for PCT/EP2006/008221, mailed Mar. 2, 2007.
Search Report as issued by the UK Patent Office (mailed Jan. 10, 2006).
Biradar et al., "Trinuclear Complexes of Dimethylsilane and Cobalt Schiff-Base Complexes." *Inorganica Chimica Acta* 74:39-41 (1983).
Opstal et al., "Easily Accessible Ring Opening Metathesis and Atom Transfer Radical Polymerization Catalysts based on Arene, Norbornadiene and Cyclooctadiene Ruthenium Complexes Bearing Schiff Base Ligands." *Adv. Synth. Catal.* 45:393-401 (2003).
Trnka et al., "The Development of $L_2X_2Ru$=CHR Olefin Metathesis Catalysts: An Organometallic Success Story." *Acc. Chem. Res.* 34:18-29 (2001).
Drozdzak et al., "Latent Olefin Metathesis Catalysts for Polymerization of DCPD," *Macromol. Symp.* 293:1-4, 2010.

Monsaert et al., "A Highly Controllable Latent Ruthenium Schiff Base Olefin Metathesis Catalyst: Catalyst Activation and Mechanistic Studies," *J. Polym. Sci. A Polym. Chem.* 48:302-310, 2010.
Bel'Skii et al., "Hydrogen Bonds of Phenol and Tert-Butyl Alcohol with Phosponic Esters," *Zhurnal Obshchei Khimii* 45(12):2606-2609 (1975).
Chang et al., "Synthesis and Characterization of New Ruthenium-Based Olefin Metathesis Catalysts Coordinated with Bidentate Schiff-Base Ligands," *Organometallics* 17: 3460-3465 (1998).
Clercq et al., "Immobilization of Multifunctional Schiff Base Containing Ruthenium Complexes on MCM-41." *Applied Catalysis A.*: General 247: 345-364 (2003).
Dieltiens et al., "Pyrrole Synthesis Using a Tandem Grubbs' Carbene-$RuCl_3$ Catalytic System," *Tetrahedron Lett.* 45: 8995-8998 (2004).
Floch et al., "Phosphonolipids as Non-Viral Vectors for Gene Therapy," *European Journal of Medicinal Chemistry* 33:923-934 (1998).
Garber et al., "Efficient and Recyclable Monomeric and Dendritic Ru-Based Metathesis Catalysts," *J. Am. Chem. Soc.* 122:8168-8179 (2000).
Gross et al., "α-Substituted Phosphonates. 37. Derivatives of α-Pyrrolomethylphosphonic Acid and N-vinylpyrroles," Chemical Abstracts [Online]: Database Accession No. 96:199787, year of 1981.
Hodgson et al., "Unsaturated 1,2-Amino Alcohols From Dihydropyrrole Epoxides and Organolithiums," *Synlett* 2:310-312 (2002).
March, "Acids and Bases," Advanced Organic Chemistry, 3$^{rd}$ Edition, Wiley, NY, 220-222, (1968).
Sanford et al., "Synthesis and Reactivity of Neutral and Cationic Ruthenium(II) Tris(pyrazolyl)borate Alkylidenes," *Organometallics* 17:5384-5389 (1998).
Toreki et al., "Metathetical Reactions of Re(VII) Alkylidene-Alkylidyne Complexes of the Type Re(CR')(CHR')[$OCMe(CF_3)_2$]$_2$ (R'=$CMe_3$ or $CMe_2Ph$) with Terminal and Internal Olefins," *Journal of the American Chemical Society* 115:127-137 (1993).
European Patent Office Communication (05447043.0-2103) dated Sep. 23, 2005.
European Search Report (EP Application No. 06020387.4-1211) dated Dec. 19, 2006.
Examiner's First Report on Australian Patent Application No. 2003236511 (Australian National Phase of PCT/BE2003/000008), dated Jan. 25, 2008, Australian Government/IP Australia.
International Preliminary Examination Report (PCT/BE 03/00008) dated Jan. 22, 2002.
International Preliminary Report on Patentability (PCT/BE2005/000030) dated Feb. 7, 2006.
International Search Report (PCT/BE2005/000030) dated Sep. 16, 2005.
Written Opinion of the International Searching Authority (PCT/BE2005/000030) dated Sep. 16, 2005.

* cited by examiner (IA)

(IB)

(II A)

(II B)

(IIIA)

(IIIB)

(IV D)

IV A

IV B (IV C)

(V A)

(V B)

MULTICOORDINATED METAL COMPLEXES FOR USE IN METATHESIS REACTIONS

This application claims priority from U.S. provisional application No. 60/710,073, filed Aug. 22, 2005 and from British patent application serial number GB 0517137.6 filed Aug. 22, 2005; the disclosures of each are hereby incorporated by reference.

The present invention relates to multicoordinated metal complexes which are useful as catalyst components, either alone or in combination with co-catalysts or initiators, in a wide variety of organic synthesis reactions including the metathesis of unsaturated compounds such as olefins and alkynes.

The present invention also relates to methods for making said multicoordinated metal complexes and to novel intermediates involved in such methods. More particularly, the present invention relates to multicoordinated complexes of metals such as but not limited to ruthenium wherein said complexes comprise a modified Schiff base ligand, as well as methods for making the same and the use of such multicoordinated metal complexes as catalysts for the metathesis of numerous unsaturated hydrocarbons such as non-cyclic mono-olefins, dienes and alkynes, in particular for the ring-opening metathesis polymerisation of cyclic olefins.

BACKGROUND OF THE INVENTION

Olefin metathesis is a catalytic process including, as a key step, a reaction between a first olefin and a first transition metal alkylidene complex, thus producing an unstable intermediate metallacyclobutane ring which then undergoes transformation into a second olefin and a second transition metal alkylidene complex according to equation (1) hereunder. Reactions of this kind are reversible and in competition with one another, so the overall result heavily depends on their respective rates and, when formation of volatile or insoluble products occur, displacement of equilibrium.

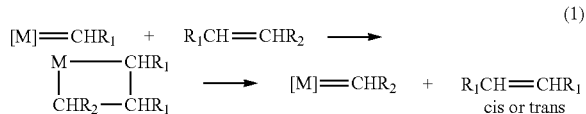

Several exemplary but non-limiting types of metathesis reactions for mono-olefins or di-olefins are shown in equations (2) to (5) herein-after. Removal of a product, such as ethylene in equation (2), from the system can dramatically alter the course and/or rate of a desired metathesis reaction, since ethylene reacts with an alkylidene complex in order to form a methylene (M=CH$_2$) complex, which is the most reactive and also the least stable of the alkylidene complexes.

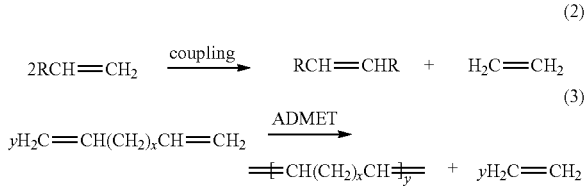

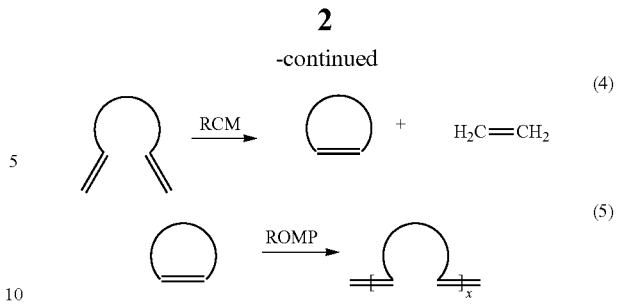

Of potentially greater interest than homo-coupling (equation 2) is cross-coupling between two different terminal olefins. Coupling reactions involving dienes lead to linear and cyclic dimers, oligomers, and, ultimately, linear or cyclic polymers (equation 3). In general, the latter reaction called acyclic diene metathesis (hereinafter referred to as ADMET) is favoured in highly concentrated solutions or in bulk, while cyclisation is favoured at low concentrations. When intramolecular coupling of a diene occurs so as to produce a cyclic alkene, the process is called ring-closing metathesis (hereinafter referred to as RCM) (equation 4). Strained cyclic olefins can be opened and oligomerised or polymerised (ring opening metathesis polymerisation (hereinafter referred to as ROMP) shown in equation 5). When the alkylidene catalyst reacts more rapidly with the cyclic olefin (e.g. a norbornene or a cyclobutene) than with a carbon-carbon double bond in the growing polymer chain, then a "living ring opening metathesis polymerisation" may result, i.e. there is little termination during or after the polymerization reaction.

A large number of catalyst systems comprising well-defined single component metal carbene complexes have been prepared and utilized in olefin metathesis. One major development in olefin metathesis was the discovery of the ruthenium and osmium carbene complexes by Grubbs and co-workers. U.S. Pat. No. 5,977,393 discloses Schiff base derivatives of such compounds, which are useful as olefin metathesis catalysts, wherein the metal is coordinated by a neutral electron donor, such as a triarylphosphine or a tri(cyclo)alkylphosphine, and by an anionic ligand. Such catalysts show an improved thermal stability while maintaining metathesis activity even in polar protic solvents. They are also able to promote cyclisation of, for instance, diallylamine hydrochloride into dihydropyrrole hydrochloride. Remaining problems to be solved with the carbene complexes of Grubbs are (i) improving both catalyst stability (i.e. slowing down decomposition) and metathesis activity at the same time and (ii) broadening the range of organic products achievable by using such catalysts, e.g. providing ability to ring-close highly substituted dienes into tri- and tetra-substituted olefins.

International patent application published as WO 99/00396 discloses at least penta-coordinated ruthenium and osmium complexes including two anionic ligands and two monodentate neutral electron donor ligands and further wherein one of the coordinating ligands is a heteroatom-containing alkylidene of the formula =CH—Z—R, wherein Z is sulfur, hydrocarbylphosphino, oxygen or hydrocarbylamino, and wherein R is hydrocarbyl.

International patent application published as WO 03/062253 discloses five-coordinate metal complexes, salt, solvates or enantiomers thereof, comprising a carbene ligand, a multidentate ligand and one or more other ligands, wherein at least one of said other ligands is a constraint steric hindrance ligand having a pKa of at least 15. More specifically, the said document discloses five-coordinate metal complexes having one of the general formulae (IA) and (IB) referred to in FIG. 1, wherein:

M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, copper, chromium, manganese, rhodium, vanadium, zinc, gold, silver, nickel and cobalt;

Z is selected from the group consisting of oxygen, sulphur, selenium, NR'''', PR'''', AsR'''' and SbR'''';

R'', R''' and R'''' are each a radical independently selected from the group consisting of hydrogen, $C_{1-6}$ alkyl, $C_{3-8}$ cycloalkyl, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, aryl and heteroaryl, or R'' and R''' together form an aryl or heteroaryl radical, each said radical (when different from hydrogen) being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, aryisulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium;

R' is either as defined for R'', R''' and R'''' when included in a compound having the general formula (IA) or, when included in a compound having the general formula (IB), is selected from the group consisting of $C_{1-6}$ alkylene and $C_{3-8}$ cycloalkylene, the said alkylene or cycloalkylene group being optionally substituted with one or more substituents $R_5$;

$R_1$ is a constraint steric hindrance group having a pKa of at least about 15;

$R_2$ is an anionic ligand;

$R_3$ and $R_4$ are each hydrogen or a radical selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium;

R' and one of $R_3$ and $R_4$ may be bonded to each other to form a bidentate ligand;

R''' and R'''' may be bonded to each other to form an aliphatic ring system including a heteroatom selected from the group consisting of nitrogen, phosphorous, arsenic and antimony;

$R_3$ and $R_4$ together may form a fused aromatic ring system, and y represents the number of $sp_2$ carbon atoms between M and the carbon atom bearing $R_3$ and $R_4$ and is an integer from 0 to 3 inclusive, salts, solvates and enantiomers thereof.

These five-coordinate metal complexes of WO 03/062253 proved to be very efficient olefin metathesis catalysts. International patent application published as WO 2005/035121 discloses at least tetra-coordinated metal complexes, salts, solvates and enantiomers thereof, comprising:

a multidentate ligand being coordinated with the metal by means of a nitrogen atom and at least one heteroatom selected from the group consisting of oxygen, sulphur, selenium, nitrogen, phosphorus, arsenic and antimony, wherein each of nitrogen, phosphorus, arsenic and antimony is substituted with a radical R'''' selected from the group consisting of hydrogen, $C_{1-7}$ alkyl, $C_{3-10}$ cycloalkyl, aryl and heteroaryl;

a non-anionic unsaturated ligand $L^1$ selected from the group consisting of aromatic and unsaturated cycloaliphatic groups, preferably aryl, heteroaryl and $C_{4-20}$ cycloalkenyl groups, the said aromatic or unsaturated cycloaliphatic group being optionally substituted with one or more $C_{1-7}$ alkyl groups or electron-withdrawing groups such as, but not limited to, halogen, nitro, cyano, (thio)carboxylic acid, (thio)carboxylic acid (thio)ester, (thio)carboxylic acid (thio)amide, (thio)carboxylic acid anhydride and (thio) carboxylic acid halide; and a non-anionic ligand $L^2$ selected from the group consisting of $C_{1-7}$ alkyl, $C_{3-10}$ cycloalkyl, aryl, arylalkyl, alkylaryl and heterocyclic, the said group being optionally substituted with one or more preferably electron-withdrawing substituents such as, but not limited to, halogen, nitro, cyano, (thio)carboxylic acid, (thio)carboxylic acid (thio)ester, (thio)carboxylic acid (thio)amide, (thio)carboxylic acid anhydride and (thio) carboxylic acid halide.

The multidentate ligand of such an at least tetra-coordinated metal complex may be a bidentate or tridentate Schiff base. WO 2005/035121 also discloses hexa-coordinated metal complexes, salts, solvates and enantiomers thereof, comprising:

a multidentate ligand being coordinated with the metal by means of a nitrogen atom and at least one heteroatom selected from the group consisting of oxygen, sulphur, selenium, nitrogen, phosphorus, arsenic and antimony, wherein each of nitrogen, phosphorus, arsenic and antimony is substituted with a radical R'''' selected from the group consisting of hydrogen, $C_{1-7}$ alkyl, $C_{3-10}$ cycloalkyl, aryl and heteroaryl;

at least one non-anionic bidentate ligand $L^3$ being different from the multidentate ligand; and at most two anionic ligands $L^4$, wherein one or more of said anionic ligands $L^4$ may be each replaced with a solvent S, in which case the said hexa-coordinated metal complex is a cationic species associated with an anion A.

The multidentate ligand of such an at least hexa-coordinated metal complex may be a bidentate or tridentate Schiff base. These tetra-coordinated and hexa-coordinated metal complexes of WO 2005/035121 proved to be very efficient olefin metathesis catalysts, especially in the ring opening metathesis polymerisation of norbornene and derivatives thereof.

However there is a continuous need in the art for improving catalyst efficiency, i.e. improving the yield of the reaction catalysed by the said catalyst component after a certain period of time under given conditions (e.g. temperature, pressure, solvent and reactant/catalyst ratio) or else, at a given reaction yield, providing milder conditions (lower temperature, pressure closer to atmospheric pressure, easier separation and purification of product from the reaction mixture) or requiring a smaller amount of catalyst (i.e. a higher reactant/catalyst ratio) and thus resulting in more economic and environment-friendly operating conditions. This need is still more stringent for use in reaction-injection molding (RIM) processes such as, but not limited to, the bulk polymerisation of endo- or exo-dicyclopentadiene, or formulations thereof.

WO 93/20111 describes osmium- and ruthenium-carbene compounds with phosphine ligands as purely thermal catalysts for ring-opening metathesis polymerization of strained cycloolefins, in which cyclodienes such as dicyclopentadiene act as catalyst inhibitors and cannot be polymerized. This is confirmed for instance by example 3 of U.S. Pat. No. 6,284,852, wherein dicyclopentadiene did not yield any polymer, even after days in the presence of certain ruthenium carbene complexes having phosphine ligands. However, U.S. Pat. No. 6,235,856 teaches that dicyclopentadiene is accessible to thermal metathesis polymerization with a single-component catalyst if carbene-free ruthenium(II)- or osmium(II)-phosphine catalysts are used.

U.S. Pat. No. 6,284,852 discloses enhancing the catalytic activity of a ruthenium carbene complex of the formula $A_xL_yX_zRu=CHR'$, wherein x=0, 1 or 2, y=0, 1 or 2, and z=1 or 2 and wherein R' is hydrogen or a substituted or unsubstituted alkyl or aryl, L is any neutral electron donor, X is any anionic ligand, and A is a ligand having a covalent structure connecting a neutral electron donor and an anionic ligand, by the deliberate addition of specific amounts of acid not present as a substrate or solvent, the said enhancement being for a variety of olefin metathesis reactions including ROMP, RCM, ADMET and cross-metathesis and dimerization reactions. According to U.S. Pat. No. 6,284,852, organic or inorganic acids may be added to the catalysts either before or during the reaction with an olefin, with longer catalyst life being observed when the catalyst is introduced to an acidic solution of olefin monomer. The amounts of acid disclosed in examples 3 to 7 of U.S. Pat. No. 6,284,852 range from 0.3 to 1 equivalent of acid, with respect to the alkylidene moiety. In particular, the catalyst systems of example 3 (in particular catalysts being Schiff-base-substituted complexes including an alkylidene ligand and a phosphine ligand) in the presence of HCl as an acid achieve ROMP of dicyclopentadiene within less than 1 minute at room temperature in the absence of a solvent, and ROMP of an oxanorbornene monomer within 15 minutes at room temperature in the presence of a protic solvent (methanol), however at monomer/catalyst ratios which are not specified.

U.S. Pat. No. 6,284,852 also shows alkylidene ruthenium complexes which, after activation in water with a strong acid, quickly and quantitatively initiate living polymerization of water-soluble polymers, resulting in a significant improvement over existing ROMP catalysts. It further alleges that the propagating species in these reactions is stable (a propagating alkylidene species was observed by proton nuclear magnetic resonance) and that the effect of the acid in the system appears to be twofold: in addition to eliminating hydroxide ions which would cause catalyst decomposition, catalyst activity is also enhanced by protonation of phosphine ligands. It is also taught that, remarkably, the acids do not react with the ruthenium alkylidene bond.

Although providing an improvement over existing ROMP catalysts, the teaching of U.S. Pat. No. 6,284,852 is however limited in many aspects, namely:
because its alleged mechanism of acid activation involves the protonation of phosphine ligands, it is limited to alkylidene ruthenium complexes including at least one phosphine ligand;
it does not disclose reacting a Schiff-base-substituted ruthenium complex with an acid under conditions such that said acid at least partly cleaves a bond between ruthenium and the Schiff base ligand of said complex.

U.S. Pat. No. 6,284,852 does not either teach the behaviour, in the presence of an acid, of ruthenium complexes wherein ruthenium is coordinated with a vinylidene ligand, an allenylidene ligand or a N-heterocyclic carbene ligand.

U.S. Pat. No. 6,284,852 therefore has left open ways for the study of multi-coordinated metal complexes, in particular multicoordinated ruthenium and osmium complexes in an acidic, preferably a strongly acidic, environment when used for olefin or alkyne metathesis reactions including ROMP, RCM, ADMET, and for cross-metathesis and dimerization reactions.

Therefore one goal of this invention is the design of new and useful catalytic species, especially based on multicoordinated transition metal complexes, having unexpected properties and improved efficiency in olefin or alkyne metathesis reactions.

Another goal of this invention is to efficiently perform olefin or alkyne metathesis reactions, in particular ring opening polymerization of strained cyclic olefins (including cationic forms of such monomers such as, but not limited to, strained cyclic olefins including quaternary ammonium salts), in the presence of multicoordinated transition metal complexes without being limited by the requirement of a phosphine ligand in said complexes.

There is also a specific need in the art, which is yet another goal of this invention, for improving reaction-injection molding (RIM) processes, resin transfer molding (RTM) processes, pultrusion, filament winding and reactive rotational molding (RRM) processes such as, but not limited to, the bulk polymerisation of endo- or exo-dicyclopentadiene, or copolymerization thereof with other monomers, or formulations thereof. More specifically there is a need to improve such processes which are performed in the presence of multicoordinated transition metal complexes, in particular ruthenium complexes, having various combinations of ligands but which do not necessarily comprise phosphine ligands. All the above needs constitute the various goals to be achieved by the present invention, nevertheless other advantages of this invention will readily appear from the following description.

SUMMARY OF THE INVENTION

In a first aspect the present invention is based on the unexpected finding that improved catalysts useful in a number of organic synthesis reactions such as, but not limited to, the metathesis of unsaturated compounds such as olefins and alkynes can be obtained by bringing into contact a multi-coordinated metal complex, preferably an at least tetra-coordinated transition metal complex comprising a multidentate Schiff base ligand and one or more other ligands (such as, but not limited to, the metal complexes of WO 03/062253 or WO 20051035121), with an activating metal or silicon compound selected from the group consisting of:
copper (I) halides,
zinc compounds represented by the formula $Zn(R_5)_2$, wherein $R_5$ is halogen, $C_{1-7}$ alkyl or aryl,
tin compounds represented by the formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl, and
silicon compounds represented by the formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl, under conditions such that at least partial cleavage of a bond between the metal and the multidentate Schiff base ligand of said multi-coordinated metal complex occurs.

In a second aspect the present invention is based on the unexpected finding that improved catalysts useful in a number of organic synthesis reactions such as, but not limited to, metathesis reactions of unsaturated organic compounds such as olefins and alkynes can be obtained by bringing into contact a multi-coordinated metal complex, preferably an at least tetra-coordinated transition metal complex comprising a multidentate Schiff base ligand and one or more other ligands (such as, but not limited to, the metal complexes of WO 03/062253 or WO 2005/035121), with an activating compound comprising at least one halogen atom directly bonded to at least one atom having an atomic mass from 27 to 124 and being selected from the group consisting of groups IB, IIB, IIIA, IVB, IVA and VA of the Periodic Table of elements under conditions such that at least partial cleavage of a bond between the metal and the multidentate Schiff base ligand of said multi-coordinated metal complex occurs. The activating compound may further comprise, depending upon the nature of the atom having an atomic mass from 27 to 124, one or more hydrogen atoms and/or one or more saturated or unsaturated hydrocarbyl groups directly bonded to said at least one atom having an atomic mass from 27 to 124. The atom having an atomic mass from 27 to 124 may be a metal or a non-metal, according to the classification of elements standard in the art.

In one specific embodiment, the present invention is based on the unexpected finding that new and useful catalytic species can be suitably obtained by reacting an activating compound such as defined herein-above with a multi-coordinated metal complex, preferably an at least tetra-coordinated transition metal complex comprising a multidentate Schiff base ligand and further comprising a set of one or more other ligands such as, but not limited to, anionic ligands, N-heterocyclic carbene ligands, alkylidene ligands, vinylidene ligands, indenylidene ligands and allenylidene ligands, wherein said set of other ligands is free from any phosphine ligand. More specifically, this invention is based on the finding that suitable conditions for the activation reaction between the activating compound and the multi-coordinated metal complex are conditions which permit, in one or several steps, the at least partial decoordination of the multidentate Schiff base ligand through cleavage of the imine bond to the metal center and optionally the coordination of the nitrogen atom of said Schiff base to the metal or silicon of the activating compound.

Based on these findings, the present invention thus provides new catalytic species or products, or mixtures of species, deriving from the reaction (hereinafter also referred as "activation") between the starting multi-coordinated Schiff-base-substituted metal complex and said activating compound. In the broader acceptance, these species may be monometallic species represented by the general formula:

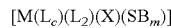

wherein
M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, copper, chromium, manganese, rhodium, vanadium, zinc, gold, silver, nickel and cobalt;
$SB_m$ is a modified Schiff base ligand, wherein modification comprises coordination of the nitrogen atom of said Schiff base to the metal or silicon atom of the activating compound;
$L_c$ is a carbene ligand, preferably selected from the group consisting of alkylidene ligands, vinylidene ligands, indenylidene ligands and allenylidene ligands;
$L_2$ is a non-anionic ligand, preferably other than a phosphine ligand; and
X is an anionic ligand,
including salts, solvates and enantiomers thereof.

These species may also be bimetallic species represented by the general formula:

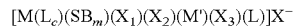

wherein
M and M' are each a metal independently selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, copper, chromium, manganese, rhodium, vanadium, zinc, gold, silver, nickel and cobalt;
$SB_m$ is a modified Schiff base ligand, wherein modification comprises coordination of the nitrogen atom of said Schiff base to the metal or silicon atom of the activating compound;
$L_c$ is a carbene ligand, preferably selected from the group consisting of alkylidene ligands, vinylidene ligands, indenylidene ligands, heteroatom-containing alkylidene ligands and allenylidene ligands;
L is a non-anionic ligand, preferably other than a phosphine ligand; and
$X_1$, $X_2$ and $X_3$ are each independently selected from anionic ligands,
including salts, solvates and enantiomers thereof.

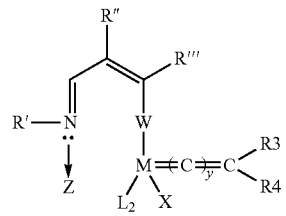

(VI)

When starting from a multi-coordinated Schiff-base-substituted monometallic complex, such new species or products may for instance take the form of one or more monometallic species being represented by the general formula (VI): or by the general formula (VII):

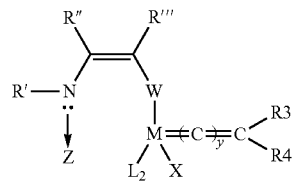

(VII)

wherein
M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, copper, chromium, manganese, rhodium, vanadium, zinc, gold, silver, nickel and cobalt;
W is selected from the group consisting of oxygen, sulphur, selenium, NR'''', PR'''', AsR'''' and SbR'''';
R'', R''' and R'''' are each a substituent independently selected from the group consisting of hydrogen, $C_{1-6}$ alkyl, $C_3$-8 cycloalkyl, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, aryl and heteroaryl, or R" and R'" together form an aryl or heteroaryl substituent, each said substituent (when different from hydrogen) being itself optionally substituted with one or more, preferably 1 to 3, substituents $R_{20}$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkylaryloxysilyl, $C_{1-6}$ alkyl-$C_{3-10}$ cycloalkoxysilyl, alkylammonium and aryl-ammonium;

R' is either as defined for R", R'" and R"" when included in a compound having the general formula (VI) or, when included in a compound having the general formula (VII), is selected from the group consisting of $C_{1-6}$ alkylene and $C_{3-8}$ cycloalkylene, the said alkylene or cycloalkylene group being optionally substituted with one or more substituents $R_{20}$ as defined herein before;

$L_2$ is a non-anionic ligand, preferably other than a phosphine ligand;

X is an anionic ligand;

$R_3$ and $R_4$ are each hydrogen or a radical selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium;

R' and one of $R_3$ and $R_4$ may be bonded to each other to form a bidentate ligand;

R'" and R"" may be bonded to each other to form an aliphatic ring system including a heteroatom selected from the group consisting of nitrogen, phosphorous, arsenic and antimony;

$R_3$ and $R_4$ together may form a fused aromatic ring system, y represents the number of $sp_2$ carbon atoms between M and the carbon atom bearing $R_3$ and $R_4$ and is an integer from 0 to 3 inclusive, and Z is an activating metal or silicon compound such as defined herein-above, including salts, solvates and enantiomers thereof.

When starting from a multi-coordinated Schiff-base-substituted bimetallic complex, such new species or products may for instance take the form of one or more bimetallic species being represented by the structural formula (X):

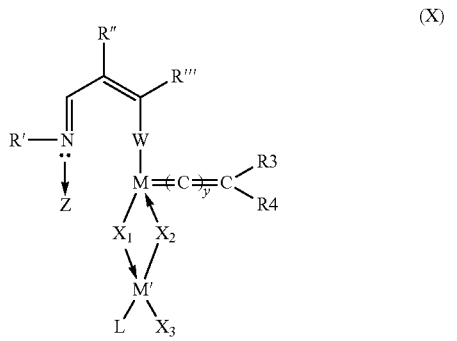

(X)

or by the structural formula (XI):

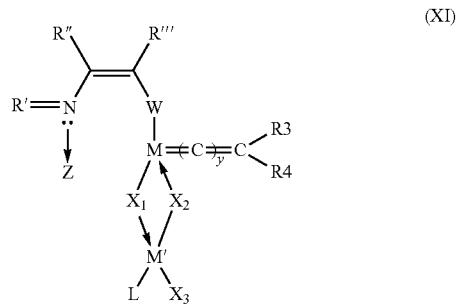

(XI)

wherein

M and M' are each a metal independently selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, copper, chromium, manganese, rhodium, vanadium, zinc, gold, silver, nickel and cobalt;

W, R', R", R'", R"", y, $R_3$ and $R_4$ are as defined in formulae (VI) and (VII) hereinabove;

$X_1$, $X_2$ and $X_3$ are each independently selected from anionic ligands,

L is a non-anionic ligand, preferably other than a phosphine ligand, and

Z is an activating metal or silicon compound such as defined herein-above, including salts, solvates and enantiomers thereof.

In another specific embodiment, the present invention is based on the unexpected finding that useful catalytic species can be suitably obtained by reacting a metal or silicon activating compound such as defined hereinabove with respect to the first aspect of the invention, provided that said metal or silicon activating compound includes at least one halogen atom, or by reacting an activating compound such as defined with respect to the second aspect of the invention, with said multi-coordinated metal complex (preferably an at least tetra-coordinated transition metal complex comprising a multidentate Schiff base ligand such as specified herein-above) in the presence of at least one further reactant being an organic acid or having the formula RYH, wherein Y is selected from the group consisting of oxygen, sulfur and selenium, and R is selected from the group consisting of hydrogen, aryl, arylalkyl, heteocyclic, heterocyclic-substituted alkyl, $C_{2-7}$ alkenyl and $C_{1-7}$ alkyl. According to this specific embodiment, a strong acid (such as a hydrogen halide) may be formed in situ by the reaction of said activating compound, e.g. metal or silicon activating compound, with said further reactant (e.g. a reactant having the formula RYH), and said strong acid if produced in sufficient amount may in turn be able:

in a first step, to protonate the multidentate Schiff base ligand and decoordinate the nitrogen atom of the imino group of said multidentate Schiff base ligand from the complexed metal, and in a second step, to decoordinate the further heteroatom of said multidentate Schiff base ligand from the complexed metal.

In this specific embodiment, at least partial cleavage of a bond between the metal and the multidentate Schiff base ligand of said multi-coordinated metal complex occurs like in the absence of the further reactant (e.g. one having the formula RYH), but coordination of the nitrogen atom of the Schiff base ligand to the metal or silicon or other atom having an atomic mass from 27 to 124 of the activating compound occurs less frequently because it competes unfavourably with the protonation/decoordination mechanism resulting from the in situ generation of a strong acid (such as a hydrogen halide). This alternative mechanism is however quite effective in the catalysis of metathesis reactions of organic compounds since it provides a more random distribution of the strong acid formed in the reaction mixture than if the same strong acid is introduced directly in the presence of the multicoordinated metal complex.

The new catalytic species of the invention may be produced extra-temporaneously, separated, purified and conditioned for separate use in organic synthesis reactions later on, or they may be produced in situ during the relevant chemical reaction (e.g. metathesis of unsaturated organic compounds) by introducing a suitable amount of the (e.g. metal or silicon) activating compound into the reaction mixture before, simultaneously with, or alternatively after the introduction of the starting Schiff base metal complex. The present invention also provides catalytic systems including, in addition to said new catalytic species or reaction products, a carrier suitable for supporting said catalytic species or reaction products.

The present invention also provides methods and processes involving the use of such new catalytic species or reaction products, or any mixture of such species, or such catalytic systems, in a wide range of organic synthesis reactions including the metathesis of unsaturated compounds such as olefins and alkynes and certain reactions involving the transfer of an atom or group to an ethylenically or acetylenically unsaturated compound or another reactive substrate, such as atom transfer radical polymerisation, atom transfer radical addition, vinylation, cyclopropanation of ethylenically unsaturated compounds, and the like. In particular, this invention provides an improved process for the ring opening polymerization of strained cyclic olefins such as, but not limited to, dicyclopentadiene.

DEFINITIONS

Figure 1:
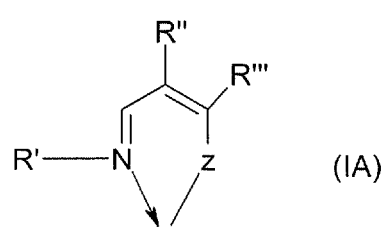
FIG. 1 shows bidentate Schiff base ligands having the general formulae (I A) and (I B) that may be included in multicoordinated metal complexes suitable for modification according to an embodiment of the present invention.
Figure 1:
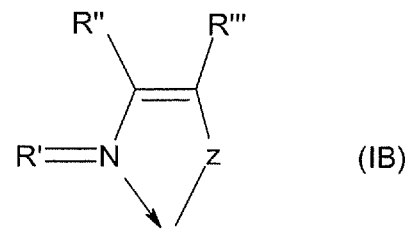

As used herein, the term complex, or coordination compound, refers to the result of a donor-acceptor mechanism or Lewis acid-base reaction between a metal (the acceptor) and several neutral molecules or ionic compounds called ligands, each containing a non-metallic atom or ion (the donor). Ligands that have more than one atom with lone pairs of electrons (i.e. more than one point of attachment to the metal center) and therefore occupy more than one coordination site are called multidentate ligands. The latter, depending upon the number of coordination sites occupied, include bidentate, tridentate and tetradentate ligands.

As used herein, the term "monometallic" refers to a complex in which there is a single metal center. As used herein, the term "heterobimetallic" refers to a complex in which there are two different metal centers. As used herein, the term "homobimetallic" refers to a complex having two identical metal centers, which however need not have identical ligands or coordination number.

As used herein with respect to a substituent, ligand or group, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (tert-butyl), 2-methylbutyl, n-pentyl, dimethylpropyl, n-hexyl, 2-methylpentyl, 3-methylpentyl, n-heptyl and the like; optionally the carbon chain length of such group may be extended to 20 carbon atoms.

As used herein with respect to a linking group, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituent, ligand or group, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_7$-10 polycyclic saturated hydrocarbon monovalent radical having from 7 to 10 carbon atoms such as, for instance, norbornyl, fenchyl, trimethyltricycloheptyl or adamantyl.

As used herein with respect to a linking group, and unless otherwise stated, the term "$C_{3-10}$ cycloalkylene" means the divalent hydrocarbon radical corresponding to the above defined $C_{3-10}$ cycloalkyl, such as 1,2-cyclohexylene and 1,4-cyclohexylene.

As used herein with respect to a substituent, ligand or group, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphtyl, fluorenyl and the like, all of the said radicals being optionally substituted with one or more substituents selected from the group consisting of halogen, amino, nitro, hydroxyl, sulfhydryl and nitro, such as for instance 4-fluorophenyl, 4-chlorophenyl, 3,4-dichlorophenyl, 2,6-diisopropyl-4-bromophenyl, pentafluorophenyl and 4-cyanophenyl.

As used herein with respect to a linking group, and unless otherwise stated, the term "arylene" means the divalent hydrocarbon radical corresponding to the above defined aryl, such as phenylene, toluylene, xylylene, naphthylene and the like.

As used herein with respect to a combination of two substituting hydrocarbon radicals, and unless otherwise stated, the term "homocyclic" means a mono- or poly-cyclic, saturated or mono-unsaturated or polyunsaturated hydrocarbon radical having from 4 up to 15 carbon atoms but including no heteroatom in the said ring; for instance the said combination forms a $C_2$-6 alkylene radical, such as tetramethylene, which cyclizes with the carbon atoms to which the said two substituting hydrocarbon radicals are attached.

As used herein with respect to a substituent (or a combination of two substituents), ligand or group, and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzooxepinyl, dibenzopyranonyl, dibenzoquinoxalinyl, dibenzothiazepinyl, dibenzoisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphtotriazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydro-quinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazinyl, benzoxazinyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, indolinyl, indolizidinyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may be independently substituted with a substituent selected from the group consisting of halogen, nitro, $C_{1-7}$ alkyl (optionally containing one or more functions or groups selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino, phenylhydrazino, sulfonyl, sulfonamido and halogen), $C_{2-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 membered ring, heterocyclic radicals may be sub-divided into heteroaromatic (or "heteroaryl") radicals and non-aromatic heterocyclic radicals; when a heteroatom of the said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituent, ligand or group, and unless otherwise stated, the terms "$C_{1-7}$ alkoxy", "$C_{2-7}$ alkenyloxy", "$C_{2-7}$ alkynyloxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a $C_1$-17 alkyl, $C_{2-7}$ alkenyl or $C_{2-7}$ alkynyl (optionally the carbon chain length of such groups may be extended to 20 carbon atoms), respectively a $C_{3-10}$ cycloalkyl, aryl, arylalkyl or heterocyclic radical (each of them such as defined herein), are attached to an oxygen atom or a divalent sulfur atom through a single bond, such as but not limited to methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy and the like.

As used herein with respect to a substituting atom or ligand, the term halogen means any atom selected from the group consisting of fluorine, chlorine, bromine and iodine.

As used herein with respect to a substituting radical or group, and unless otherwise stated, the term "halo $C_{1-7}$ alkyl" means a $C_{1-7}$ alkyl radical (such as above defined, i.e. optionally the carbon chain length of such group may be extended to 20 carbon atoms) in which one or more hydrogen atoms are independently replaced by one or more halogens (preferably fluorine, chlorine or bromine), such as but not limited to fluoromethyl, difluoromethyl, trifluoromethyl, chloromethyl, dichloromethyl, trichloromethyl, 2,2,2-trifluoroethyl, 2-fluoroethyl, 2-chloroethyl, 2,2,2-trichloroethyl, octafluoropentyl, dodecafluoroheptyl, dichloromethyl and the like.

As used herein with respect to a substituent, ligand or group, and unless otherwise stated, the term "$C_{2-7}$ alkenyl" means a straight or branched acyclic hydrocarbon monovalent radical having one or more ethylenical unsaturations and having from 2 to 7 carbon atoms such as, for example, vinyl, 1-propenyl, 2-propenyl (allyl), 1-butenyl, 2-butenyl, 3-butenyl, 2-pentenyl, 3-pentenyl, 3-methyl-2-butenyl, 3-hexenyl, 2-hexenyl, 2-heptenyl, 1,3-butadienyl, n-penta-2,4-dienyl, hexadienyl, heptadienyl, heptatrienyl and the like, including all possible isomers thereof; optionally the carbon chain length of such group may be extended to 20 carbon atoms (such as n-oct-2-enyl, n-dodec-2-enyl, isododecenyl, n-octadec-2-enyl and n-octadec-4-enyl).

As used herein with respect to a substituent, ligand or group, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, 1,3,5,7-cyclooctatetraenyl and the like, or a $C_7$-10 polycyclic mono- or polyunsaturated hydrocarbon monovalent radical having from 7 to 10 carbon atoms such as dicyclopentadienyl, fenchenyl (including all isomers thereof, such as α-pinolenyl), bicyclo[2.2.1]hept-2-enyl (norbornenyl), bicyclo[2.2.1]hepta-2,5-dienyl (norbornadienyl), cyclofenchenyl and the like.

As used herein with respect to a substituent, ligand or group, the term "$C_{2-7}$ alkynyl" defines straight and branched chain hydrocarbon radicals containing one or more triple bonds (i.e. acetylenic unsaturation) and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like, including all possible isomers thereof; optionally the carbon chain length of such group may be extended to 20 carbon atoms.

As used herein with respect to a substituent, ligand or group, and unless otherwise stated, the terms "arylalkyl", "arylalkenyl" and "heterocyclic-substituted alkyl" refer to an aliphatic saturated or unsaturated hydrocarbon monovalent radical (preferably a $C_{1-7}$ alkyl or $C_{2-7}$ alkenyl radical such as defined above, i.e. optionally the carbon chain length of such group may be extended to 20 carbon atoms) onto which an aryl or heterocyclic radical (such as defined above) is already bonded, and wherein the said aliphatic radical and/or the said aryl or heterocyclic radical may be optionally substituted with one or more substituents selected from the group consisting of halogen, amino, nitro, hydroxyl, sulfhydryl and nitro, such as but not limited to benzyl, 4-chlorobenzyl, phenylethyl, 3-phenylpropyl, α-methylbenzyl, phenbutyl, α,α-dimethylbenzyl, 1-amino-2-phenylethyl, 1-amino-2-[4-hydroxyphenyl]ethyl, 1-amino-2-[indol-2-yl]ethyl, styryl, pyridylmethyl, pyridylethyl, 2-(2-pyridyl)isopropyl, oxazolylbutyl, 2-thienylmethyl and 2-furylmethyl.

As used herein with respect to a substituent, ligand or group, and unless otherwise stated, the terms "alkylcycloalkyl", "alkenyl(hetero)aryl", "alkyl(hetero)aryl" and "alkyl-substituted heterocyclic" refer respectively to an aryl, heteroaryl, cycloalkyl or heterocyclic radical (such as defined above) onto which are already bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above, such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, lutidinyl (i.e. dimethylpyridyl), 2-methylaziridinyl, methylbenzimidazolyl, methylbenzofuranyl, methylbenzothiazolyl, methylbenzotriazolyl, methylbenzoxazolyl, methylcyclohexyl and menthyl.

As used herein with respect to a substituent or group, and unless otherwise stated, the terms "alkylamino", "cycloalkylamino", "alkenylamino", "cycloalkenylamino", "arylamino", "aryl-alkylamino", "heterocyclic amino", "hydroxyalkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic, mono- or polyhydroxy $C_{1-7}$ alkyl, mono- or polymercapto $C_{1-7}$ alkyl or $C_{2-7}$ alkynyl radical(s) (each of them as defined herein, respectively) is/are attached to a nitrogen atom through a single bond or, in the case of heterocyclic, include a nitrogen atom, such as but not limited to, anilino, benzylamino, methylamino, dimethylamino, ethylamino, diethylamino, isopropylamino, propenylamino, n-butylamino, tert-butylamino, dibutylamino, morpholinoalkylamino, morpholinyl, piperidinyl, piperazinyl, hydroxymethylamino, β-hydroxyethylamino and ethynylamino; this definition also includes mixed disubstituted amino radicals wherein the nitrogen atom is attached to two such radicals belonging to two different sub-set of radicals, e.g. an alkyl radical and an alkenyl radical, or to two different radicals within the same sub-set of radicals, e.g. methylethylamino; among disubstituted amino radicals, symetrically substituted are usually preferred and more easily accessible.

As used herein, and unless otherwise stated, the terms "(thio)carboxylic acid (thio)ester" and "(thio)carboxylic acid (thio)amide" refer to substituents wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of $C_{1-7}$ alkyl, $C_{2-7}$ alkenyl, $C_{2-7}$ alkynyl, $C_{3-10}$ cycloalkyl, $C_{3-10}$ cycloalkenyl, aryl, arylalkyl, alkylaryl, alkylamino, cycloalkylamino, alkenylamino, cycloalkenylamino, arylamino, arylalkylamino, heterocyclic amino, hydroxyalkylamino, mercapto-alkylamino or alkynylamino (each such as above defined, respectively).

As used herein with respect to a metal ligand, the terms alkylammonium and aryl-ammonium mean a tetra-coordinated nitrogen atom being linked to one or more $C_{1-7}$ alkyl, $C_{3-10}$ cycloalkyl, aryl or heteroaryl groups, each such as above defined, respectively.

As used herein with respect to a metal ligand, and unless otherwise stated, the term "Schiff base" conventionally refers to the presence of an imino group (usually resulting from the reaction of a primary amine with an aldehyde or a ketone) in the said ligand, being part of a multidentate ligand (such as defined for instance in http://www.ilpi.comlorganomet/coordnum.html) and which is coordinated to the metal, in addition to the nitrogen atom of said imino group, through at least one further heteroatom selected from the group consisting of oxygen, sulfur and selenium. The said multidentate ligand may be for instance:
- a N,O-bidentate Schiff base ligand such as a lumazine or substituted lumazine or 2-(2-hydroxyphenyl)benzoxazole or (2'-hydroxyphenyl)-2-thiazoline, or
- a N,S-bidentate Schiff base ligand such as a thiolumazine or substituted thiolumazine, or
- a N,Z-bidentate Schiff base ligand such as shown in FIG. 1, wherein Z is or includes an atom selected from the group consisting of oxygen, sulfur and selenium; it may be advantageous for the said bidentate Schiff base ligand to further include a carbon-carbon double bond conjugated with the carbon-nitrogen double bond of the imino group, for instance as shown in FIG. 1, or
- a N,N,O— tridentate Schiff base ligand such as derived from 6-amino-5-formyl-1,3-dimethyluracil and semicarbazide or acetylhydrazine or benzoylhydrazine, or such as derived from 7-formyl-8-hydroxyquinoline(oxine) and 2-aminophenol or 2-aminopyridine, or
- a O,N,O-tridentate Schiff base ligand such as 6-amino-5-formyl-1,3-dimethyluracilbenzoyl-hydrazone or such as shown in formula (IV) of FIG. 5 or N-(2-methoxyphenyl)salicylideneamine or salicylaldehyde-2-hydroxanil or the heterocyclic Schiff base resulting from the reaction of 1-amino-5-benzoyl-4-phenyl-1H pyrimidin-2-one with 2-hydroxynaphtaldehyde or the thenoyltrifluoroaceto antipyrine Schiff base resulting from the reaction of thenoyl-trifluoroacetone with 4-aminoantipyrine, or
- a O,N,S-tridentate Schiff base ligand such as salicylaldehyde-2-mercaptoanil, S-benzyl-2-[(2-hydroxyphenyl) methylene]dithiocarbazate or 2-[(2-hydroxyphenyl) methylene]-N-phenylhydrazinecarbothioamide, or
- a N,N,S-tridentate Schiff base ligand such as 6-amino-5-formyl-1,3-dimethyluracilthio-semicarbazonate.

Figure 2:
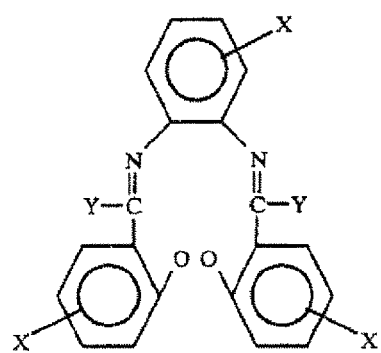
FIG. 2 shows tetradentate Schiff base ligands having the general formulae (II A) and (II B) that may be included in multicoordinated metal complexes suitable for modification according to another embodiment of the present invention.
Figure 2:
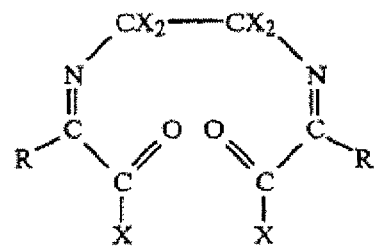
Figure 3:
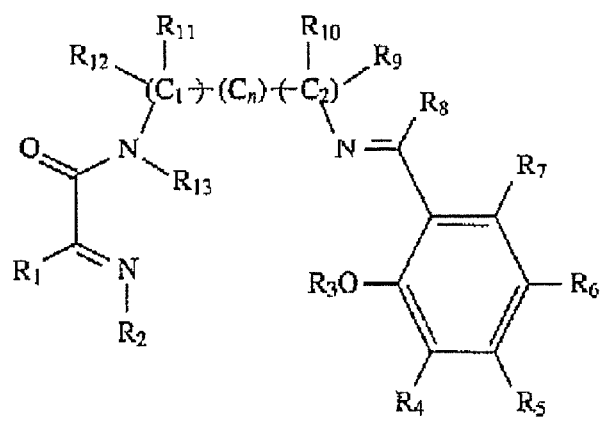
FIG. 3 shows tetradentate Schiff base ligands having the general chemical formulae (III A) and (III B) that may be included in multicoordinated metal complexes suitable for modification according to this invention.
Figure 3:
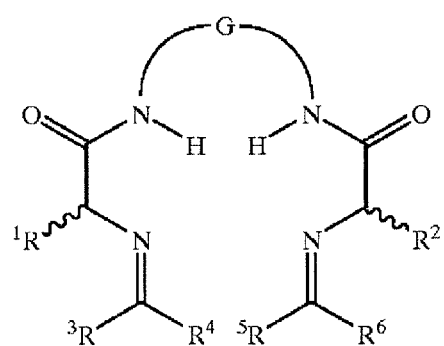

By extension, the multidentate ligand may include more than one Schiff base, for instance two imino groups as shown in formulae (IIA) and (IIB) of FIG. 2 and in formula (IIIA) of FIG. 3, thus possibly resulting in O,N,N,O-tetradentate or O,N,N,N-tetradentate Schiff base ligands.

As used herein, the term "heteroatom-containing alkylidene" relates to ligands of the formula =CH—Z—R, wherein Z is sulfur, hydrocarbylphosphino, oxygen or hydrocarbylamino, and wherein R is hydrocarbyl, such as described for instance in WO 99/00396.

As used herein, the term "constraint steric hindrance" relates to a group or ligand, usually a branched or substituted group or ligand, which is constrained in its movements, i.e. a group the size of which produces a molecular distortion (either an angular distortion or a lengthening of bonds) being measurable by X-ray diffraction.

As used herein and unless otherwise stated, the term "stereoisomer" refers to all possible different isomeric as well as conformational forms which the compounds of the invention may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a compound of this invention with a suitable inorganic solvent (e.g. hydrates formed with water) or organic solvent, such as but not limited to alcohols (in particular ethanol and isopropanol), ketones (in particular methylethylketone and methylisobutylketone), esters (in particular ethyl acetate) and the like.

DETAILED DESCRIPTION OF THE INVENTION

In its broadest meaning, the present invention first relates to a method of modifying a multi-coordinated metal complex, a salt, a solvate or an enantiomer thereof, said multi-coordinated metal complex preferably comprising (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) one or more other ligands, under conditions such that at least partial cleavage of a bond between the metal and the multidentate Schiff base ligand of said multi-coordinated metal complex occurs. The metal complex modification occurs by reaction with an activating compound, and may further optionally include:
- either the coordination of the nitrogen atom of said Schiff base to the activating compound,
- or the protonation of said multidentate Schiff base ligand, optionally followed by decoordination of said further heteroatom of said multidentate Schiff base ligand from the complexed metal,
- or both.

In order to achieve this result, i.e. in order to effectively modify the structure of a starting multi-coordinated metal complex and preferably in order to modify said structure in such a way that the catalytic efficiency of the modified metal complex is higher than the catalytic efficiency of the starting non-modified metal complex in a given organic reaction such as the metathesis of unsaturated organic compounds, the activating compound must be suitably selected. According to the first aspect of the present invention, the activating compound must be selected within the groups of metal or silicon activating compounds described hereinabove in the summary of the invention together with reference to specific formulae. For practical reasons it is preferred to use such compounds that are commercially available and, when such compounds are solid at room temperature, to use solutions of such compounds in suitable organic solvents such as, but not limited to, ethers (e.g. diethyl ether or tetrahydrofuran), alcanes, aromatic hydrocarbons (e.g. toluene), esters (e.g. alkyl acetates), halogenated hydrocarbons and the like. Also for practical reasons for further use of the modified metal complex in organic synthesis reactions such as the metathesis of unsaturated compounds (e.g. olefins and alkynes), it is preferred that said organic solvents be the same as, or at least miscible with the organic solvent, if any, to be used for performing said organic synthesis reactions. The skilled person can readily determine, from general literature (such as the *Handbook of Chemistry and Physics* (e.g. $61^{th}$ edition, 1980) or from standard solubility tests, which solvents are most appropriate for each individual activating compound.

Copper (I) halides suitable as activating compounds in this invention include, but are not limited to, copper (I) bromide, copper (I) chloride, copper (I) fluoride, copper (I) iodide and copper (I) fluosilicate $Cu_2SiF_6$.

Zinc compounds suitable as activating compounds in the first aspect of this invention include, but are not limited to, di-n-butylzinc, diethylzinc, dimethylzinc, diphenylzinc, di-n-propylzinc, di-o-tolylzinc and zinc bromide, zinc chloride, zinc fluoride and zinc iodide.

Tin compounds suitable as activating compounds in the first aspect of this invention include, but are not limited to, di-n-butyltin dibromide, di-n-butyltin dichloride, di-tert-butyltin dichloride, dimethyltin dibromide, dimethyltin dichloride, dimethyltin difluoride, dimethyltin diiodide, diphenyltin dichloride, diphenyltin dibromide, diphenyltin difluoride, diphenyltin diiodide, tributyltin fluoride, tributyltin chloride, tributyltin bromide, tributyltin iodide, phenyltin tribromide, phenyltin trichloride, tricyclohexyltin chloride, triethyltin bromide, triethyltin chloride, triethyltin iodide, vinyltributyltin, tetrabutyltin, tin (IV) bromide, tin bromide trichloride, tin dibromide dichloride, tin tribromide chloride, tin dibromide, diiodide, tin (IV) chloride, tin trichloride bromide, tin dichloride diiodide, tin (IV) fluoride, tin (IV) iodide, butyltin trichloride, n-butylvinyltin dichloride, diallyidibutyltin, diallyldiphenyltin, dibutylvinyltin bromide, dibutylvinyltin chloride, dichlorodi-m-tolylstannane, diethyldiisoamyltin, diethyldiisobutyltin, diethyldiphenyltin, diethylisoamyltin bromide, diethylisoamyltin chloride, diethylisobutyltin bromide, diethyl-n-propyltin bromide, diethyl-n-propyltin chloride, diethyl-n-propyltin fluoride, diethyltin dibromide, diethyltin dichloride, diethyltin difluoride, diethyltin diiodide, diisoamyltin dibromide, diisoamyltin dichloride, diisoamyltin diiodide, diisobutyltin dichloride, diisobutyltin diiodide, diisopropyltin dichloride, diisopropyltin dibromide, dimethyldiethyltin, dimethyldiisobutyltin, dimethyldioctyltin, dimethyldivinyltin, dimethylethylpropyltin, dimethylethyltin iodide, dimethyldivinyltin, dimethylvinyltin bromide, dimethylvinyltin iodide, diphenyldivinyltin, dipropyltin difluoride, dipropyltin diiodide, dipropyltin dichloride, dipropyltin dibromide, di-o-tolyltin dichloride, di-p-tolyltin dichloride, ditriphenyl-stannylmethane, divinylbutyltin chloride, divinyltin dichloride, ethyldiisoamyltin bromide, ethyldiisobutyltin bromide, ethylmethylpropyltin iodide, ethyl-n-propyldiisoamyltin, ethylpropyltin dichloride, ethyltin tribromide, ethyltin triiodide, ethyltri-n-butyltin, ethyltri-n-propyltin, methyltin tribromide, methyltin trichloride, methyltin triiodide, methyltri-n-butyltin, methyltri-n-propyltin, phenylbenzyltin dichloride, phenyltribenzyltin, propyltin triiodide, propyltri-n-amyltin, tetra-n-amyltin, tetra-n-butyltin, tetrabenzyltin, tetracyclohexyltin, tetraethyltin, tetra-n-heptyltin, tetra-n-hexyltin, tetraisoamyltin, tetraisobutyltin, tetralauryltin, tetramethyltin, tetra-n-octyltin, tetraphenyltin, tetrapropyltin, tetra-o-tolyltin, tetra-m-tolyltin, tetra-p-tolyltin, tetravinyltin, tetra-m-xylyltin, tetra-p-xylyltin, o-tolyltin trichloride, p-tolyltin trichloride, m-tolyltrichlorostannane, triallylbutyltin, tri-n-amyltin bromide, tribenzylethyltin, tribenzyltin chloride, tribenzyltin iodide, tri-n-butyltin bromide, tri-n-butylvinyltin, triethyl-n-amyltin, triethylisoamyltin, triethylisobutyltin, triethylphenyltin, triethyl-n-propyltin, triisoamyltin bromide, triisoamyltin chloride, triisoamyltin fluoride, triisoamyltin iodide, triisobutylethyltin, triisobutylisoamyltin, triisobutyltin bromide, triisobutyltin chloride, triisobutyltin fluoride, triisobutyltin iodide, triisopropyltin bromide, triisopropyltin iodide, trimethyldecyltin, trimethyldodecyltin, trimethylethyltin, trimethyltin bromide, trimethyltin chloride, trimethyltin fluoride, trimethyltin iodide, triphenylallyltin, triphenylbenzyltin, triphenylbutyltin, triphenylethyltin, triphenylmethyltin, triphenyl-α-naphthyltin, triphenyltin bromide, triphenyltin chloride, triphenyltin fluoride, triphenyltin iodide, triphenyl-p-tolyltin, triphenyl-p-xylyltin, tri-n-propyl-n-butyltin, tri-n-propylethyltin, tri-n-propylisobutyl tin, tri-n-propyltin chloride, tri-n-propyltin fluoride, tri-n-propyltin iodide, tri-o-tolyltin bromide, tri-p-tolyltin bromide, tri-o-tolyltin chloride, tri-m-tolyltin chloride, tri-p-tolyltin chloride, tri-p-tolyltin fluoride, tri-o-tolyltin iodide, tri-p-tolyltin iodide, triphenylstannylmethane, trivinyidecyltin, trivinylhexyltin, trivinyloctyltin, trivinyltin chloride, vinyltin trichloride, tri-p-xylyltin bromide, tri-p-xylyltin chloride, tri-p-xylyltin fluoride, tri-p-xylyltin iodide and tri-m-xylyltin fluoride.

Silicon compounds suitable as activating compounds in the first aspect of this invention include, but are not limited to, bromosilane, dibromosilane, bromotrichlorosilane, dibromodichlorosilane, chlorosilane, dichlorosilane, dichlorodifluorosilane, trichlorosilane, trichloroiodosilane, trifluorosilane, triiodosilane, iodosilane, dimethylhexylsilyl chloride, dimethylphenylsilane, dimethylethylsilane, diethylmethylsilane, dichlorodiphenylsilane, diphenylmethylsilane, diphenylsilane, dichlorodiethylsilane, methylsilane, methyltriphenylsilane, tetraphenylsilane, tributylsilane, tetraethylsilane, tetramethylsilane, silicon tetrachloride, ethyltrichloro-silane, octyltrichlorosilane, octadecyltrichlorosilane, phenyltrichlorosilane, triethylsilane, triethylfluorosilane, triethylvinylsilane, triisobutylsilane, triisopropylsilane, triisopropylsilyl chloride, vinyltrichlorosilane, vinyltrimethylsilane, chlorotrimethylsilane, bromotrimethylsilane, 2-trimethylsilyl-1,3-dithiane, iodotrimethylsilane, chlorodimethylethylsilane, chlorodimethylisopropylsilane, chlorodimethyloctadecylsilane, chlorodimethyloctylsilane, chlorodimethylphenylsilane, chlorocyclohexyldimethylsilane, butyltrifluorosilane, chloro(3-cyanopropyl)dimethylsilane, chloro(chloromethyl)-dimethylsilane, (chloromethyl)trichlorosilane and chlorodimethylpentafluorophenylsilane.

According to the second aspect of the invention, the activating compound must include at least one halogen atom directly bonded to at least one atom having an atomic mass from 27 to 124 and being selected from the group consisting of groups IB, IIB, IIIA, IVB, IVA and VA of the Periodic Table of elements. Preferred such atoms include aluminium (atomic mass 27), silicium (atomic mass 28), phosphorus (atomic mass 31), titanium (atomic mass 48), copper (atomic mass 63), zinc (atomic mass 65), and tin (atomic mass 119 or 124). Other suitable atoms include antimony, germanium, cadmium, silver, indium and zirconium.

When such atom having an atomic mass from 27 to 124 is copper, it may be any copper (I) halide as described herein with respect to the first aspect of the invention.

When such atom having an atomic mass from 27 to 124 is zinc, it may be any zinc halide as described herein with respect to the first aspect of the invention.

When such atom having an atomic mass from 27 to 124 is tin or silicon, it may be any tin compound or silicon compound as described herein with respect to the first aspect of the invention, provided that said tin compound or silicon compound includes at least a halogen atom. In particular it may be any tin compound represented by the structural formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl, provided that at least one of $R_9$, $R_{10}$, $R_{11}$, and $R_{12}$ is halogen. It may also be any silicon compound represented by the structural formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl, provided that at least one of $R_{13}$, $R_{14}$, $R_{15}$ and $R_{16}$ is halogen.

Titanium compounds suitable as activating compounds in the second aspect of this invention include titanium tetrahalides such as titanium tetrachloride and titanium tetrabromide, and titanium trichloride.

Phosphorous compounds suitable as activating compounds in the second aspect of this invention include phosphorous halides, oxyhalides and thiohalides such as, but not limited to, phosphorous pentabromide, tribromide, dibromide trichloride, monobromide tetrachloride, pentachloride, trichloride, dichloride trifluoride, trichloride diiodide, pentafluoride, trifluoride, triiodide, oxybromide, oxychloride, oxyfluoride, thiobromide and thiochloride.

Aluminium compounds suitable as activating compounds in the second aspect of this invention may be represented by the structural formula $AlR_{17}R_{18}R_{19}$ wherein each of $R_9$, $R_{17}$, $R_{18}$ and $R_{19}$ is independently selected from the group consisting of halogen, hydrogen and $C_{1-7}$ alkyl, provided that at least one of $R_{17}$, $R_{18}$ and $R_{19}$ is halogen. Non limiting examples include aluminium halides such as bromide, chloride, fluoride and iodide; dialkylaluminum halides such as diethylaluminum chloride and dimethylaluminum chloride; and alkylaluminum dihalides such as methylaluminium dichloride.

Other compounds suitable as activating compounds in the second aspect of this invention include, but are not limited to:
- antimony compounds such as antimony oxychloride, triethyl antimony dichloride, and triphenyl antimony dichloride; and
- germanium compounds which may be represented by the structural formula $GeR_{20}R_{21}R_{22}R_{23}$ wherein each of $R_{20}$, $R_{21}$, $R_{22}$ and $R_{23}$ is independently selected from the group consisting of halogen, $C_{1-7}$ alkyl, aryl and arylalkyl, provided that at least one of $R_{20}$, $R_{21}$, $R_{22}$ and $R_{23}$ is halogen.

In order to achieve the desired metal complex modification, not only the activating compound must be suitably selected but also it is important to properly select its molar ratio to the multi-coordinated metal complex to be modified, as well as the other operating conditions of the modification reaction. Preferably, said conditions independently include one or more of the following:
- a molar ratio between said activating compound and the metal of said multi-coordinated metal complex being above about 5:1, preferably above about 10:1, more preferably above about 20:1, for instance at least about 30:1;
- a molar ratio between said activating compound and the metal of said multi-coordinated metal complex being not above about 2000:1, preferably not above about 500:1, and more preferably not above about 250:1;
- a contact time above 5 seconds, preferably above 30 seconds, more preferably at least 1 minute, for example at least 5 minutes;
- a contact time below 100 hours, preferably not above 24 hours, more preferably not above 4 hours, and most preferably not above 2 hours;
- a contact temperature from about −50° C. to about 80° C., preferably from about 10° C. to about 60° C., more preferably from about 20° C. to about 50° C.

According to a first embodiment of this invention, the activating compound is used as the single species for modifying a multi-coordinated metal complex (or a salt, a solvate or an enantiomer thereof). As will be understood from the following description, this means that when the activating compound includes at least one halogen atom, it is not used in the presence of an additive such as water, an organic acid, an alcohol or a phenol that can abstract said halogen atom and replace the activating compound with another activating species. Such additives to be avoided for performing the first embodiment of this invention include, but are not limited to:
- impurities of the solvent that may be used for performing a metathesis reaction in the presence of the multi-coordinated metal complex,
- impurities of the unsaturated compound that may be submitted to a metathesis reaction in the presence of the multi-coordinated metal complex, and
- additives (e.g. antioxidants) deliberately present in the unsaturated compound that may be submitted to a metathesis reaction in the presence of the multi-coordinated metal complex.

According to a second embodiment of this invention, the metal complex modification takes place in the further presence of a reactant being an organic acid or having the formula RYH, wherein Y is selected from the group consisting of oxygen, sulfur and selenium, preferably Y is oxygen, and R is selected from the group consisting of hydrogen, aryl, heterocyclic, heterocyclic-substituted alkyl, arylalkyl, $C_{2-7}$ alkenyl and $C_{1-7}$ alkyl. In order for this specific embodiment to provide additional useful effect over the embodiment without said further reactant, especially by forming in situ a strong acid (such as a hydrogen halide) by the reaction of the activating compound with said further reactant (e.g. a reactant having the formula RYH), it is however necessary for the activating compound to include at least one halogen atom. The further reactant present in this embodiment of the invention thus has at least one labile hydrogen atom, such as water, monocarboxylic acids, monohydric alcohols and phenols, but may also have more than one labile hydrogen atom, such as polycarboxylic acids (in particular dicarboxylic acids), polyhydric alcohols, alcohols/phenols and polyphenols. Since water is also a further reactant according to this embodiment of the invention, it is not necessary for these mono- or polycarboxylic acids, monohydric or polyhydric alcohols, phenols or polyphenols to be used in strictly anhydrous grades but it is admissible to use them in the form of commercial grades including traces of water. Preferably the further reactant has no other functional group that may negatively interact with the hydrogen halide formation process, e.g. by providing the possibility for a competitive reaction with the halogen atom of the activating compound and thus slowing down the rate of the desired hydrogen halide formation. Therefore it may be important to purify a commercial grade of the further reactant when it is known or suspected to contain a significant amount of at least one impurity having such negatively interacting functional group. For practical reasons it is preferred to use reactants that are commercially available and, when such reactants are solid at room temperature, to use solutions of such reactants in suitable organic solvents such as, but not limited to, ethers (e.g. diethyl ether or tetrahydrofuran), alcanes, aromatic hydrocarbons (e.g. toluene) and the like. Also for practical reasons for further use of the modified metal complex in organic synthesis reactions such as the metathesis of unsaturated compounds (e.g. olefins and alkynes), it is preferred that said organic solvents be the same as, or at least miscible with the organic solvent, if any, to be used for performing said organic synthesis reactions. The skilled person can readily determine, from general literature (such as the *Handbook of Chemistry and Physics* (e.g. $61^{th}$ edition, 1980) or from standard solubility tests, which solvents are most appropriate for each individual further reactant.

Representative examples of suitable reactants of this type thus include, but are not limited to, the following:

$C_{1-7}$ alkyl monoalcohols such as methanol, ethanol, isopropanol, n-propanol, isobutanol, n-butanol, tert-butanol, pentanol, 2,2-dimethyl-3-pentanol, 2,3-dimethyl-3-pentanol, 2,4-dimethyl-3-pentanol, 4,4-dimethyl-2-pentanol, 2,2-dichloroethanol, 1,3-dibromo-2-propanol, 2,3-dibromopropanol, 1,3-dichloro-2-propanol, 1,3-dichloro-2-propanol, 2-chloroethanol, 2-(2-chloroethoxy)ethanol, 2-[(2-chloroethoxy)ethoxy]-ethanol, 6-chloro-1-hexanol, 2-chloromethyl-2-methyl-1-propanol, 1-bromo-2-propanol, 3-bromo-1-propanol, 3-methyl-1-butanol, 2,2,2-tribromoethanol, 2,2,2-trifluoroethanol, 2,2,2-trichloroethanol, 2,2,3,3,3-pentafluoro-1-propanol, 2,2,3,3,4,4,4-heptafluoro-1-butanol, 1-heptanol and 2-heptanol;

$C_{2-7}$ alkenyl monoalcohols such as 3-methyl-3-buten-1-ol, allyl alcohol, 3-buten-1-ol, 3-buten-2-ol, 1-hexen-3-ol, 2-hexen-1-ol, 4-hexen-1-ol, 5-hexen-1-ol and the like;

$C_{2-7}$ alkenyl polyalcohols such as 2-butene-1,4-diol and the like, $C_{1-7}$ alkyl polyalcohols such as ethanediol, 1,2-propanediol, 1,2-propanediol, 1,2-butane-diol, 1,3-butanediol, 1,4-butanediol, 2,3-butanediol, 2,4-dimethyl-2,4-pentanediol, 3-bromo-1,2-propanediol, 1,2-pentanediol, 1,4-pentanediol, 1,5-pentanediol, 1,5-hexanediol, 1,6-hexanediol, 2,5-hexanediol, 1,7-heptanediol, 1,2,4-butanetriol, 1,2,6-hexanetriol, mannitol and 1,2,3-heptanetriol;

arylalkyl monoalcohols such as benzyl alcohol, 2,4-dichlorobenzyl alcohol, 2,5-dichlorobenzyl alcohol, 2,6-dichlorobenzyl alcohol, 3,4-dichlorobenzyl alcohol, 3,5-dichlorobenzyl alcohol, 2,3-difluorobenzyl alcohol, 2,4-difluorobenzyl alcohol, 2,5-difluorobenzyl alcohol, 2,6-difluorobenzyl alcohol, 3,4-difluorobenzyl alcohol, 3,5-difluorobenzyl alcohol, 4,4'-difluorobenzhydrol, 2-chloro-6-fluorobenzyl alcohol, 4-bromophenethyl alcohol, 4-chlorophenethyl alcohol, 3-chlorophenethyl alcohol, 2-chlorophenethyl alcohol, 2-bromobenzyl alcohol, 3-bromobenzyl alcohol, 4-bromobenzyl alcohol, 4-isopropylbenzyl alcohol, 2,3,4,5,6-pentafluorobenzyl alcohol, and phenethyl alcohol;

phenols such as phenol, 2-benzylphenol, 4-benzylphenol, 4,4'-thiodiphenol, 3,3'-thiodipropanol, 2,2'-thiodiethanol, 4-hydroxythiophenol, 2,3-dimethylphenol, 2,4-dimethylphenol, 2,5-dimethylphenol, 2,6-dimethylphenol, 3,4-dimethylphenol, 3,5-dimethylphenol, 2,6-di-tert-butyl-4-sec-butylphenol, 2,4-dibromophenol, 2,6-dibromophenol, 2,3-dichlorophenol, 2,4-dichlorophenol, 2,5-dichlorophenol, 2,6-dichlorophenol, 3,4-dichlorophenol, 3,5-dichlorophenol, 2,3-difluorophenol, 2,4-difluorophenol, 2,5-difluorophenol, 2,6-difluorophenol, 3,4-difluorophenol, o-cresol, m-cresol, p-cresol, 2-fluorophenol, 3-fluorophenol, 4-fluorophenol, 2-chloro-4-fluorophenol, 3-chloro-4-fluorophenol, 4-chloro-2-fluorophenol, 4-chloro-3-fluorophenol, 2-chloro-4-methylphenol, 2-chloro-5-methylphenol, 4-chloro-2-methylphenol, 4-chloro-3-methylphenol, 2-chlorophenol, 3-chlorophenol, 4-chlorophenol, 2-bromophenol, 3-bromophenol, 4-bromophenol, 2-sec-butylphenol, 2-tert-butylphenol, 3-tert-butylphenol, 4-tert-butylphenol, 4-sec-butylphenol, 2-tert-butyl-4-methylphenol, 2-tert-butyl-5-methylphenol, 2-tert-butyl-6-methylphenol, 2-isopropylphenol, 3-isopropylphenol, 4-isopropylphenol, 4-isopropyl-3-methylphenol, 5-isopropyl-3-methylphenol, 5-isopropyl-2-methylphenol, 2-isopropoxyphenol, 2,4,6-trimethylphenol, pentafluorophenol, pentachlorophenol, 2,3,4-trichlorophenol, 2,3,5-trichlorophenol, 2,4,5-trichlorophenol, 2,4,6-trichlorophenol, 2,3,6-trichlorophenol, 2,4,6-tribromophenol, 2,3,5-trifluorophenol, 2-trifluoromethylphenol, 3-trifluoromethylphenol, 1-naphthol, 2-naphthol and 4-trifluoromethylphenol;

alcohols/phenols such as 2-hydroxybenzyl alcohol, 3-hydroxybenzyl alcohol, 4-hydroxybenzyl alcohol, 2-hydroxy-3-methoxybenzyl alcohol, 3-hydroxy-4-methoxybenzyl alcohol, 4-hydroxy-3-methoxybenzyl alcohol, 3-(4-hydroxyphenyl)-1-propanol, 2-hydroxyphenethyl alcohol, 3-hydroxyphenethyl alcohol, 2-(2-hydroxyethoxy)phenol and 4-hydroxyphenethyl alcohol;

heterocyclic-substituted alkyl alcohols such as 4-(2-hydroxyethyl)morpholine, 1-(2-hydroxyethyl)pyrrolidine, 1-piperidineethanol, 2-piperidineethanol, 4-piperidineethanol, 2-piperidinemethanol, 3-piperidinemethanol, 1-(2-hydroxyethyl)piperazine and 2-(2-hydroxyethyl)pyridine;

heterocyclic-substituted alcohols such as 3-hydroxy-1-methylpiperidine, 4-hydroxy-1-methylpiperidine, 2-hydroxy-6-methylpyridine, 5-hydroxy-2-methylpyridine, 2-hydroxypyridine, 3-hydroxypyridine, 4-hydroxypyridine and 3-hydroxytetrahydrofuran;

monocarboxylic aliphatic or aromatic acids or anhydrides such as, but not limited to, acetic acid, tribromoacetic acid, trifluoroacetic acid, trifluoroacetic anhydride, propanoic acid, butanoic acid, acetic anhydride, benzoic acid, trichlorobenzoic acid, trifluorobenzoic acid, naphthoic acid, and the like; and dicarboxylic aliphatic or aromatic acids or anhydrides such as, but not limited to, phthalic acid, phthalic anhydride, tetrahydrophthalic anhydride, maleic acid, maleic anhydride, and the like.

Within each above sub-class of suitable reactants, it may be important to pay attention to steric hindrance around the reactive carboxylic acid, alcohol or phenol group, since it is known that bulky groups such as, but not limited to, tert-butyl in the neighbourhood of said carboxylic acid, alcohol or phenol group may significantly reduce reactivity with the activating compound and, consequently, may significantly reduce the reaction rate of the metal complex modification, thus in turn resulting in slower reactivity with the unsaturated compound (such as olefin or alkyne) that is submitted to a metathesis reaction in the presence of the modified multicoordinated metal complex. This parameter may be suitably used in two ways:

when the unsaturated compound is highly reactive under the selected reaction conditions and thus involves a risk of loosing control of the reaction, it may be appropriate to select a strongly sterically hindered further reactant such as 2-tert-butylphenol, 2,6-di-tert-butyl-4-sec-butylphenol and the like, or when the unsaturated compound is hardly reactive under the selected reaction conditions, it may be appropriate to promote the desired reaction by avoiding sterically hindered further reactants or even linear or unsubstituted reactants.

In order to achieve the desired metal complex modification of this second embodiment of the invention, not only the further reactant must be suitably selected according to the above recommendations but also it is important to properly select its molar ratio to the activating compound, as well as the other operating conditions of the modification reaction. Preferably, said conditions include one or more of the following:

a molar ratio between said further reactant and said metal or silicon activating compound being such that each labile hydrogen atom of the further reactant (e.g. RYH or an organic acid) is able to react with each halogen atom of the metal or silicon activating compound; i.e. the suitable molar ratio depends upon the number of halogen atoms in the metal or silicon activating compound (which may be 1 when said activating compound is a copper (I) halide, 2 when said activating compound is a zinc compound, and from 1 to 4 when said activating compound is a silicon compound or a tin compound) and depends upon the number of labile hydrogen atoms in the further reactant (which may be 1 when said further reactant is a monocarboxylic acid, a phenol, a $C_{1-7}$ alkyl monoalcohol or an arylalkyl monoalcohol, or which may be 2 or more when said further reactant is a polycarboxylic acid, an alcohol/phenol or a $C_{1-7}$ alkyl polyalcohol), thus a significant number of situations is likely to appear but in any situation the skilled is able to easily determine the proper molar ratio between the two reactive species that will provide a halogen hydride in situ;

a contact time and/or a contact temperature similar to those specified in the previous embodiment of this invention.

It should be understood that any combination of the above reaction conditions is contemplated as being within the framework of the present invention, and that the more suitable conditions depend upon the activating compound used and optionally upon the set of ligands around the metal center, especially upon the Schiff base ligand, but the more suitable combination of reaction parameters can easily be determined by the skilled person while performing standard optimization experimentation, based on the information contained therein.

Certain phenols, in particular substituted phenols such as 2,6-di-tert-butyl-4-sec-butylphenol, are frequently used as antioxidants in commercial grades of some unsaturated compounds (such as olefins or alkynes) that may be submitted to a metathesis reaction in the presence of a modified multicoordinated metal complex according to this invention. In such a situation, the second embodiment of the invention is necessarily applicable and it is advisable to determine the exact amount of such substituted phenols being present in the unsaturated compound in order to calculate the suitable amount of activating compound to be used, taking into account the desired molar ratio between the reactive phenol and the activating compound, as well as the amount of the multicoordinated metal complex to be used as a catalyst for the metathesis reaction.

In the broadest meaning of the invention, the multicoordinated metal complex to be modified is not critical but preferably includes (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) one or more other ligands. When the second embodiment of the invention is applicable, said other ligands (ii) are preferably not selected from the group consisting of amines, phosphines, arsines and stibines, since all of the latter are able of protonation by a hydrogen halide under the above reaction conditions.

For the performance of the method of the invention, with respect to the definition of the ligands coordinating the metal center, the latter is not a critical parameter but it is suitable when at least one of the following situations occurs:

at least one of said other ligands (ii) is a constraint steric hindrance ligand having a pKa of at least 15, the number of carbon atoms in said at least one multidentate Schiff base ligand (i), between the nitrogen atom of said imino group and said coordinating heteroatom of said at least one multidentate Schiff base ligand (i), is 2 or 3, the nitrogen atom of the imino group of the multidentate Schiff base ligand (i) is substituted with a group having substantial steric hindrance such as tert-butyl, substituted phenyl (e.g. mesityl or 2,6-dimethyl-4-bromophenyl) or $C_{3-10}$ cycloalkyl (e.g. adamantyl), at least one of said other ligands (ii) is a carbene ligand, preferably selected from the group consisting of N-heterocyclic carbene ligands, alkylidene ligands, vinylidene ligands, indenylidene ligands, heteroatom-containing alkylidene ligands, and allenylidene ligands, at least two of said other ligands (ii) are carbene ligands, preferably including one selected from the group consisting of alkylidene ligands, vinylidene ligands, indenylidene ligands, heteroatom-containing alkylidene ligands and allenylidene ligands, and a second one being a N-heterocyclic carbene ligand, at least one of said other ligands (ii) is an anionic ligand, at least one of said other ligands (ii) is a non-anionic ligand, e.g. one other than a carbene ligand.

It should be understood that any combination of the above conditions is contemplated as being within the framework of the present invention, and that the more suitable conditions can easily be determined by the skilled person based on the general knowledge in the art and on information contained therein. Apart from the above-stated exception for amines, phosphines, arsines and stibines, usually the number and kind of said other ligands (ii) does not play a significant role in the feasability or efficiency of the metal complex modification according to the invention.

In a second aspect, the present invention relates to a reaction product of:

(a) a multi-coordinated metal complex, a salt, a solvate or an enantiomer thereof, said multi-coordinated metal complex comprising (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) one or more other ligands, and (b) an activating metal or silicon compound selected from the group consisting of:

copper (I) halides, zinc compounds represented by the formula $Zn(R_5)_2$, wherein $R_5$ is halogen, $C_{1-7}$ alkyl or aryl, aluminum compounds represented by the formula $AlR_6R_7R_8$ wherein each of $R_6$, $R_7$ and $R_8$ is independently selected from the group consisting of halogen and $C_{1-7}$ alkyl, tin compounds represented by the formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl, and silicon compounds represented by the formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl.

Such a reaction product is the direct result of the metal complex modification method of the first aspect (especially its first embodiment and its second embodiment) of the invention, and suitable activating metal or silicon compounds (b) are as described herein-above with respect to said modification method. The direct result of the metal complex modification method of the second embodiment of the invention is a reaction product of:

said multi-coordinated metal complex (a), an activating metal or silicon compound (b) including at least one halogen atom, and (c) a reactant being an organic acid (such as defined hereinabove) or having the structural formula RYH, wherein Y is selected from the group consisting of oxygen, sulfur and selenium, preferably Y is oxygen, and R is selected from the group consisting of hydrogen, aryl, heteocyclic, heterocyclic-substituted alkyl, arylalkyl and $C_{1-7}$ alkyl.

In the latter situation, it is preferred that said one or more other ligands (ii) of the multi-coordinated metal complex (a) are selected such as to be unable of protonation by a hydrogen halide, i.e. are not selected from the group consisting of amines, phosphines, arsines and stibines.

Figure 4:
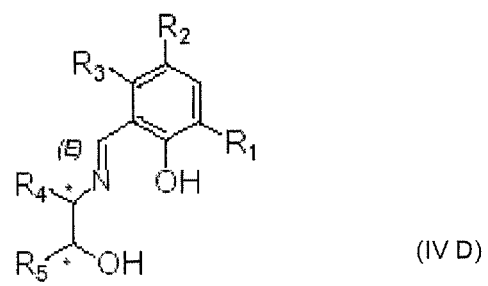
FIG. 4 shows tridentate Schiff base ligands having the general chemical formulae (IV D) that may be included in multicoordinated metal complexes suitable for modification according to the present invention.
Figure 4:
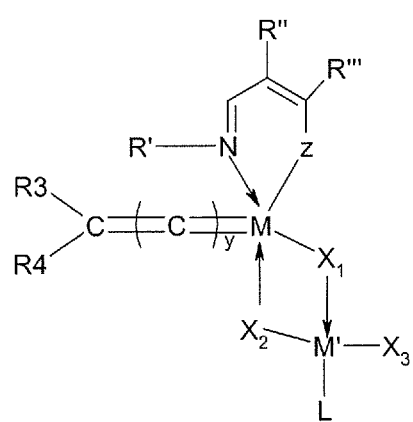
Figure 4:
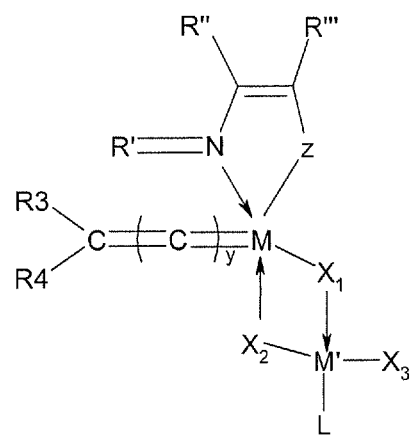
Figure 4:
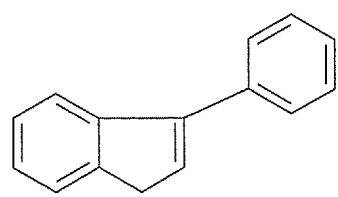

For a more detailed definition of the reaction product according to this aspect of the invention, it is preferred when at least one of the following situations occurs:

the pKa of said at least one multidentate Schiff base ligand (i) is higher than the pKa of the hydrogen halide resulting from the reaction of (b) and (c), the number of carbon atoms in said at least one multidentate Schiff base ligand (i), between the nitrogen atom of said imino group and said heteroatom of said at least one multidentate Schiff base ligand (i), is 2 or 3, at least one of said other ligands (ii) of said multi-coordinated metal complex (a) is a constraint steric hindrance ligand having a pKa of at least 15, the nitrogen atom of the imino group of the multidentate Schiff base ligand (i) is substituted with a group having substantial steric hindrance such as tert-butyl, substituted phenyl (e.g. mesityl or 2,6-dimethyl-4-bromophenyl) or $C_{3-10}$ cycloalkyl (e.g. adamantyl), at least one of said other ligands (ii) of said multi-coordinated metal complex (a) is a carbene ligand, preferably being selected from the group consisting of N-heterocyclic carbene ligands, alkylidene ligands, vinylidene ligands, indenylidene ligands, heteroatom-containing alkylidene ligands and allenylidene ligands, at least two of said other ligands (ii) are carbene ligands, preferably including one selected from the group consisting of alkylidene ligands, vinylidene ligands, indenylidene ligands, heteroatom-containing alkylidene ligands and allenylidene ligands, and a second one being a N-heterocyclic carbene ligand, at least one of said other ligands (ii) of said multi-coordinated metal complex (a) is an anionic ligand, at least one of said other ligands (ii) of said multi-coordinated metal complex (a) is a non-anionic ligand, e.g. one other than a carbene ligand, said multi-coordinated metal complex (a) is a bimetallic complex (the two metals being the same or being different), in which case preferably (1) one metal of said bimetallic complex is penta-coordinated with said at least one multidentate Schiff base ligand (i) and with said one or more other ligands (ii), and the other metal is tetra-coordinated with one or more neutral ligands and one or more anionic ligands, or (2) each metal of said bimetallic complex is hexa-coordinated with said at least one multidentate Schiff base ligand (i) and with said one or more other ligands (ii);

said multi-coordinated metal complex (a) is a monometallic complex, the metal of said multi-coordinated metal complex (a) is a transition metal selected from the group consisting of groups 4, 5, 6, 7, 8, 9, 10, 11 and 12 of the Periodic Table, for instance a metal selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt;

said multi-coordinated metal complex (a) is a penta-coordinated metal complex or a tetra-coordinated metal complex, for instance wherein (1) said at least one multidentate Schiff base ligand (i) is a bidentate ligand and said multi-coordinated metal complex (a) comprises two other ligands (ii), or wherein (2) said at least one multidentate Schiff base ligand (i) is a tridentate ligand and said multi-coordinated metal complex (a) comprises a single other ligand (ii);

said at least one multidentate Schiff base ligand (i) has one of the general formulae (IA) and (IB) referred to in FIG. 1, wherein:

Z is selected from the group consisting of oxygen, sulfur and selenium;

R" and R'" are each a radical independently selected from the group consisting of hydrogen, $C_{1-7}$ alkyl, $C_{3-10}$ cycloalkyl, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, aryl and heteroaryl, or R" and R'" together form an aryl or heteroaryl radical, each said radical being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium;

R' is either as defined for R" and R'" when included in a compound having the general formula (IA) or, when included in a compound having the general formula (IB), is selected from the group consisting of $C_{1-7}$ alkylene and $C_{3-10}$ cycloalkylene, the said alkylene or cycloalkylene group being optionally substituted with one or more substituents $R_5$;

at least one of said other ligands (ii) of said multi-coordinated metal complex (a) is a derivative, wherein one or more hydrogen atoms is substituted with a group providing constraint steric hindrance, of a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazolin-2-ylidene) bis(imidazolidin-2-ylidene), pyrrolylidene, pyrazolylidene, dihydropyrrolylidene, pyrrolylidinylidene and benzo-fused derivatives thereof, or a non-ionic prophosphatrane superbase;

at least one of said other ligands (ii) of said multi-coordinated metal complex (a) is an anionic ligand selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_1$-8 alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium, arylammonium, halogen, $C_{1-20}$ alkyldiketonate, aryldiketonate, nitro and cyano;

at least one of said other ligands (ii) of said multi-coordinated metal complex (a) is a carbene ligand represented by the general formula $=[C=]_y CR_3 R_4$, wherein:

y is an integer from 0 to 3 inclusive, and $R_3$ and $R_4$ are each hydrogen or a hydrocarbon radical selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium; or $R_3$ and $R_4$ together may form a fused aromatic ring system such as, but not limited to, one having the formula (IVC) referred to in FIG. 4, i.e. such as a phenylindenylidene ligand;

said at least one multidentate Schiff base ligand (i) is a tetradentate ligand and said multi-coordinated metal complex (a) comprises one or two other ligands (ii) being non-anionic ligands $L^7$ selected from the group consisting of aromatic and unsaturated cycloaliphatic groups, preferably aryl, heteroaryl and $C_{4-20}$ cycloalkenyl groups, wherein the said aromatic or unsaturated cycloaliphatic group is optionally substituted with one or more $C_{1-7}$ alkyl groups or electron-withdrawing groups such as, but not limited to, halogen, nitro, cyano, (thio)carboxylic acid, (thio)carboxylic acid (thio)ester, (thio)carboxylic acid (thio)amide, (thio)carboxylic acid anhydride and (thio) carboxylic acid halide;

The present invention will now be described with respect to a few preferred embodiments of the multicoordinated metal complex (a) to be modified by reaction with an activating metal or silicon compound (b), optionally in the presence of a further reactant (c) being an organic acid (such as defined hereinabove) or having the structural formula RYH.

A first species of a multicoordinated metal complex (a) suitable for reaction according to this invention with an activating metal or silicon compound (b), optionally in the presence of a reactant (c) being an organic acid or having the structural formula RYH, is a five-coordinate metal complex, a salt, a solvate or an enantiomer thereof, such as disclosed in WO 03/062253 i.e. comprising a carbene ligand, a multidentate ligand and one or more other ligands, wherein:

at least one of said other ligands (ii) is a constraint steric hindrance ligand having a pKa of at least 15 (said pKa being measured under standard conditions, i.e. at about 25° C. usually in dimethylsulfoxide (DMSO) or in water depending upon the solubility of the ligand), the multidentate ligand is a multidentate Schiff base ligand comprising an imino group and being coordinated to the metal, in addition to the nitrogen atom of said imino group, through at least one further heteroatom selected from the group consisting of oxygen, sulfur and selenium, and said other ligands (ii) are preferably unable of protonation by hydrogen halide.

The five-coordinate metal complex of this first species may be either a monometallic complex or a bimetallic complex wherein one metal is penta-coordinated and the other metal is tetra-coordinated with one or more neutral ligands and one or more anionic ligands. In the latter case, the two metals M and M' may be the same or different. Specific examples of such a bimetallic complexes are shown in the general formulae (IVA) and (IVB) referred to in FIG. 4, wherein:

Z, R', R" and R''' are as previously defined with respect to formulae (IA) and (IB), M and M' are each a metal independently selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt;

y represents the number of $sp_2$ carbon atoms between M and the carbon atom bearing $R_3$ and $R_4$ and is an integer from 0 to 3 inclusive;

$R_3$ and $R_4$ are each hydrogen or a radical selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium;

R' and one of $R_3$ and $R_4$ may be bonded to each other to form a bidentate ligand;

$X_1$, $X_2$ and $X_3$ are anionic ligands as defined below;

L is a neutral electron donor; and $R_3$ and $R_4$ together may form a fused aromatic ring system, i.e. a phenylindenylidene ligand, including salts, solvates and enantiomers thereof.

The multidentate Schiff base ligand included in this first species (a) may be either:

a bidentate Schiff base ligand, in which case the multicoordinated metal complex (a) comprises two other ligands, or a tridentate Schiff base ligand, in which case the multicoordinated metal complex (a) comprises a single other ligand.

Preferably the metal in a five-coordinate metal complex (a) of this invention is a transition metal selected from the group consisting of groups 4, 5, 6, 7, 8, 9, 10, 11 and 12 of the Periodic Table. More preferably the said metal is selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt.

The carbene ligand in a five-coordinate metal complex (a) of this invention may be an alkylidene ligand, a benzylidene ligand, a vinylidene ligand, an indenylidene ligand, a heteroatom-containing alkylidene ligand, a phenylindenylidene ligand, an allenylidene ligand or a cumulenylidene ligand, e.g. buta-1,2,3-trienylidene, penta-1,2,3,4-tetraenylidene and the like, i.e. from 1 to 3 $sp_2$ carbon atoms may be present between the metal M and the group-bearing carbon atom.

Methods for making five-coordinate metal complexes ($a_1$) according to this first species of the invention are already extensively disclosed in WO 03/062253.

A second species of a multicoordinated metal complex ($a_2$) suitable for reaction according to this invention with an activating metal or silicon compound (b) optionally in the presence of a reactant (c) being an organic acid or having the general formula RYH is a four-coordinate monometallic complex comprising a multidentate ligand and one or more other ligands, wherein:

- at least one of said other ligands (ii) is a constraint steric hindrance ligand having a pKa of at least 15, or is a group selected from aromatic and unsaturated cycloaliphatic, preferably aryl and $C_{4-20}$ cycloalkenyl (such as cyclooctadienyl, norbornadienyl, cyclopentadienyl and cyclooctatrienyl) groups, the said group being optionally substituted with one or more $C_{1-7}$ alkyl groups,
- the multidentate ligand is a multidentate Schiff base ligand comprising an imino group and being coordinated to the metal, in addition to the nitrogen atom of said imino group, through at least one further heteroatom selected from the group consisting of oxygen, sulfur and selenium, and
- said other ligands (ii) are preferably unable of protonation by hydrogen halide.

Alike in the first species, one of said other ligands (ii) present in the four-coordinate monometallic complex of this second species of the invention may be an anionic ligand such as defined previously.

More specifically, the constraint steric hindrance ligand having a pKa of at least 15 that may be included in a multicoordinated metal complex (a) may be a derivative, wherein one or more hydrogen atoms is substituted with a group providing constraint steric hindrance, of the following groups:

imidazol-2-ylidene (pKa=24),
dihydroimidazol-2-ylidene (pKa higher than 24),
oxazol-2-ylidene,
triazol-5-ylidene,
thiazol-2-ylidene,
pyrrolylidene (pKa=17.5),
pyrazolylidene,
dihydropyrrolylidene,
pyrrolylidinylidene (pKa=44),
bis(imidazoline-2-ylidene) and bis(imidazolidine-2-ylidene),
benzo-fused derivatives such as indolylidene (pKa=16), and
non-ionic prophosphatrane superbases, namely as described in U.S. Pat. No. 5,698,737, preferably trimethyltriazaprophosphatrane $P(CH_3NCH_2CH_2)_3N$ known as Verkade superbase.

The constraint steric hindrance group being present in such ligand may be for instance a branched or substituted group, e.g. a ter-butyl group, a substituted $C_{3-10}$ cycloalkyl group, an aryl group having two or more $C_{1-7}$ alkyl substituents (such as 2,4,6-trimethylphenyl (mesityl), 2,6-dimethylphenyl, 2,4,6-triisopropylphenyl or 2,6-diisopropyl-phenyl), or a heteroaryl group (such as pyridinyl) having two or more $C_{1-7}$ alkyl substituents.

As previously indicated, the multidentate Schiff base ligand (i) included either in the five-coordinate metal complex of the first species or in the four-coordinate monometallic complex of the second species may have one of the general formulae (IA) and (IB) referred to in FIG. 1, with Z, R', R" and R'" being as defined above. In the definition of the ligands having the general formula (IA), the group R' is preferably selected from methyl, phenyl and substituted phenyl (e.g. dimethylbromophenyl or diisopropylphenyl). In the definition of the ligands having the general formula (IB), the group R' is preferably methylidene or benzylidene.

Methods for making four-coordinate monometallic complexes ($a_2$) according to this second species are already extensively disclosed in WO 03/062253.

A third species of a multicoordinated metal complex ($a_3$) suitable for reaction according to this invention with an activating metal or silicon compound (b), optionally in the presence of a reactant (c) being an organic acid or having the general formula RYH, is an at least tetra-coordinated metal complex, a salt, a solvate or an enantiomer thereof, comprising:

- a multidentate Schiff base ligand (i) comprising an imino group and being coordinated to the metal, in addition to the nitrogen atom of said imino group, through at least one further heteroatom selected from the group consisting of oxygen, sulfur and selenium;
- a non-anionic unsaturated ligand $L^1$ selected from the group consisting of aromatic and unsaturated cycloaliphatic groups, preferably aryl, heteroaryl and $C_{4-20}$ cycloalkenyl groups, the said aromatic or unsaturated cycloaliphatic group being optionally substituted with one or more $C_{1-7}$ alkyl groups or with electron-withdrawing groups such as, but not limited to, halogen, nitro, cyano, (thio)carboxylic acid, (thio)carboxylic acid (thio)ester, (thio)carboxylic acid (thio)amide, (thio)carboxylic acid anhydride and (thio) carboxylic acid halide; and
- a non-anionic ligand $L^2$ selected from the group consisting of $C_{1-7}$ alkyl, $C_{3-10}$ cycloalkyl, aryl, arylalkyl, alkylaryl and heterocyclic, the said group being optionally substituted with one or more preferably electron-withdrawing substituents such as, but not limited to, halogen, nitro, cyano, (thio)carboxylic acid, (thio)carboxylic acid (thio)ester, (thio)carboxylic acid (thio)amide, (thio)carboxylic acid anhydride and (thio) carboxylic acid halide, provided that said other ligands $L^1$ and $L^2$ are unable of protonation by hydrogen halide.

In this third species ($a_3$), the multidentate ligand (i) is preferably a N,O-bidentate Schiff base ligand or N,S-bidentate Schiff base ligand, most preferably a bidentate Schiff base ligand as shown in formulae (IA) or (IB) in FIG. 1 and described in more detail hereinabove, in which case the metal complex is tetra-coordinated. The multidentate ligand (i) may also be a tridentate Schiff base, in which case the metal complex is penta-coordinated.

The at least tetra-coordinated metal complex ($a_3$) according to this third species is preferably a monometallic complex. Preferably the metal is a transition metal selected from the group consisting of groups 4, 5, 6, 7, 8, 9, 10, 11 and 12 of the Periodic Table. More preferably, said metal is selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt.

Each of the metal, the ligand $L^1$ and the ligand $L^2$ may, independently from each other, be any of the above-mentioned metals or any of the above-mentioned groups with any of the substituents listed for such groups, including any of the individual meanings for such groups or substituents which are listed in the definitions given hereinabove. Preferably the non-anionic ligand $L^2$ has constraint steric hindrance such as, but not limited to, tert-butyl, neopentyl and mono- or polysubstituted phenyl, e.g. pentafluorophenyl. $L^2$ may also be a linear $C_{1-7}$ alkyl such as methyl, or an aryl such as phenyl. Preferably the non-anionic unsaturated ligand $L^1$ also has constraint steric hindrance (such as, but not limited to, alkylaryl and alkylheteroaryl, e.g. xylyl, cumenyl or mesityl).

The at least tetra-coordinated metal complex ($a_3$) according to this third species may for instance, but without limitation, be made according to the following procedure: a metal (e.g. thallium) salt of the multidentate ligand (e.g. the bidentate or tridentate Schiff base) is first reacted with a preferably bimetallic metal complex of the desired metal, more preferably a homobimetallic complex wherein the desired metal is coordinated with a non-anionic unsaturated ligand $L^1$ and at least one anionic ligand, such as $[RuCl_2(p-cymene)]_2$, $[RuCl_2(COD)]_2$ or $[RuCl_2(NBD)]_2$, wherein COD and NBD respectively mean cyclooctadiene and norbornadiene. After removal of the metal salt formed with the anionic ligand, e.g. thallium chloride, the intermediate complex produced, i.e. a complex wherein the desired metal is coordinated with a non-anionic unsaturated ligand $L^1$, the multidentate ligand (e.g. the bidentate or tridentate Schiff base) and an anionic ligand, is reacted with a combination of the non-anionic ligand $L^2$ and an alcali or alcaline-earth metal, e.g. a $C_{1-7}$ alkyllithium, a $C_{1-7}$ alkylsodium, phenyllithium, or a Grignard reagent such as phenylmagnesium chloride, phenylmagnesium bromide or pentafluorophenylmagnesium chloride. Recovery of the desired at least tetra-coordinated metal complex of the third embodiment of the invention may suitably be achieved by removal of the alcali or alcaline-earth metal salt formed with the anionic ligand, followed by purification using conventional techniques. High yields of the pure at least tetra-coordinated metal complex of this embodiment may thus be achieved in a simple two-steps method.

A fourth species of a multicoordinated metal complex ($a_4$) suitable for reaction according to this invention with an activating metal or silicon compound (b), optionally in the presence of a reactant (c) being an organic acid or having the general formula RYH, is a hexa-coordinated metal complex, a salt, a solvate or an enantiomer thereof, comprising:
  a multidentate Schiff base ligand (i) comprising an imino group and being coordinated to the metal, in addition to the nitrogen atom of said imino group, through at least one further heteroatom selected from the group consisting of oxygen, sulfur and selenium;
  at least one non-anionic bidentate ligand $L^3$ being different from the multidentate ligand; and
  at most two anionic ligands $L^4$,
provided that said ligands $L^3$ and $L^4$ are unable of protonation by hydrogen halide.

Said hexa-coordinated metal complex (a) is preferably a bimetallic complex wherein each metal is hexa-coordinated. The two metals may be the same or different. Preferably each metal is a transition metal selected from the group consisting of groups 4, 5, 6, 7, 8, 9, 10, 11 and 12 of the Periodic Table. More preferably each said metal is independently selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt.

The multidentate ligand (i) is preferably defined as in the previous embodiments of the invention, i.e. preferably is a bidentate or tridentate Schiff base. The non-anionic bidentate ligand $L^3$ is preferably a polyunsaturated $C_{3-10}$ cycloalkenyl group such as, but not limited to, norbornadiene, cyclooctadiene, cyclopentadiene, cyclohexadiene, cycloheptadiene or cycloheptatriene, or a heteroaryl group such as defined hereinabove (preferably wherein the heteroatom is not nitrogen, phosphorus, arsenic or antimony in order to avoid a risk of protonation by the acid used for modifying the metal complex), for instance (but without limitation) a 1-hetero-2,4-cyclopentadiene such as furan or thiophene, or a fused-ring derivative thereof such as benzofuran, thienofuran or benzothiophene, or a six-membered heteroaromatic compound such as pyran or a fused-ring derivative thereof such as cyclopentapyran, chromene or xanthene. Each anionic ligand $L^4$ is preferably selected from the group consisting of $C_{1-20}$ carboxylate, $C_{1-20}$ alkoxy, $C_{2-20}$ alkenyloxy, $C_{2-20}$ alkynyloxy, aryloxy, $C_{1-20}$ alkoxycarbonyl, $C_{1-7}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium, arylammonium, alkyldiketonate (e.g. acetylacetonate), aryl-diketonate, halogen, nitro and cyano, each of the said groups being as defined above. When said hexa-coordinated metal complex is monometallic, it preferably has only one anionic ligand $L^4$.

The hexa-coordinated metal complex ($a_4$) according to this fourth species may for instance, but without limitation, be made in high yield and purity in a one-step procedure, wherein a metal (e.g. thallium) salt of the multidentate ligand (e.g. the bidentate or tridentate Schiff base) is reacted with a preferably bimetallic metal complex of the desired metal, more preferably a homobimetallic complex wherein the desired metal is coordinated with a non-anionic bidentate ligand $L^3$ and at least one anionic ligand, such as $[RuCl_2L^3]_2$, e.g. $[RuCl_2(COD)]_2$ or $[RuCl_2(NBD)]_2$, wherein COD and NBD respectively mean cyclooctadiene and norbornadiene. After removal of the metal salt formed with the anionic ligand, e.g. thallium chloride, the desired hexa-coordinated metal complex (a) may be purified using conventional techniques.

More specifically, both the at least tetra-coordinated metal complex ($a_3$) of the third species and the hexa-coordinated metal complex ($a_4$) of the fourth species may have, as a multidentate ligand (i), a bidentate Schiff base having one of the general formulae (IA) or (IB) referred to in FIG. 1, wherein Z, R', R" and R'" are as previously defined. In this specific case, preferably R" and R'" together form a phenyl group which may be substituted with one or more preferably branched alkyl groups such as isopropyl or tert-butyl. The class of bidentate Schiff bases having the general formula (IA) is well known in the art and may be made for instance by condensing a salicylaldehyde with a suitably substituted aniline. The class of bidentate Schiff bases having the general formula (IB) may be made for instance by condensing benzaldehyde with a suitably selected amino-alcohol such as o-hydroxyaniline (when Z is oxygen), an amino-thiol (when Z is sulfur).

A fifth embodiment of a multicoordinated metal complex ($a_5$) suitable for reaction according to this invention with an activating metal or silicon compound (b), optionally in the presence of a reactant (c) being an organic acid or having the general formula RYH, is an at least penta-coordinated metal complex, a salt, a solvate or an enantiomer thereof, comprising:
  a tetradentate ligand (i) comprising two Schiff bases, wherein the nitrogen atoms of said two Schiff bases are linked with each other through a $C_{1-7}$ alkylene or arylene linking group A; and
  one or more non-anionic ligands $L^7$ selected from the group consisting of aromatic and unsaturated cycloaliphatic groups, preferably aryl, heteroaryl and $C_{4-20}$ cycloalkenyl groups, wherein the said aromatic or unsaturated cycloaliphatic group is optionally substituted with one or more $C_{1-7}$ alkyl groups or electron-withdrawing groups such as, but not limited to, halogen, nitro, cyano, (thio)carboxylic acid, (thio)carboxylic acid (thio)ester, (thio)carboxylic acid (thio)amide, (thio)carboxylic acid anhydride and (thio)carboxylic acid halide.

Each of the ligand $L^7$ and the substituting groups may, independently from each other, be any of the above-mentioned groups, including any of the individual meanings for such groups or substituents which are listed in the definitions given hereinabove. Preferably the non-anionic ligand $L^7$ has constraint steric hindrance such as, but not limited to, mono- or polysubstituted phenyl, e.g. xylyl, cumenyl, cymenyl or mesityl.

The at least penta-coordinated metal complex (as) according to this fifth species preferably is a monometallic complex. Preferably the metal is a transition metal selected from the group consisting of groups 4, 5, 6, 7, 8, 9, 10, 11 and 12 of the Periodic Table. More preferably the said metal is selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt.

More specifically, in such at least penta-coordinated metal complexes ($a_5$) of the fifth species, each said non-anionic ligand $L^7$ may be cymene, and the $C_{1-7}$ alkylene or arylene linking group A may be substituted with one or more substituents preferably selected from the group consisting of chloro, bromo, trifluoromethyl and nitro. Preferably the $C_{1-7}$ alkylene or arylene linking group A, together with the two linked nitrogen atoms, is derived from o-phenylenediamine, ethylenediamine, 1,3-diaminopropane, 1,4-diaminobutane, 1,5-diaminopentane, 1,6-diaminohexane or 1,7-diaminoheptane. Also preferably, each Schiff base of the tetradentate ligand (i) is derived from salicylaldehyde or acetylacetone, wherein the salicylidene or acetylidene group included in each such Schiff base may be substituted with one or more substituents preferably selected from the group consisting of chloro, bromo, trifluoromethyl and nitro.

Suitable but non limiting examples of tetradentate ligands (i) within the scope of this fifth species have one of the general formulae (IIA) and (IIB) shown in FIG. 2. More specific examples include the so-called salen (i.e. bis(salicylaldehyde) ethylenediamine), saloph (i.e. bis(salicylaldehyde)o-phenylenediamine), hydroxy-acetoph, and accac (i.e. bis (acetylacetone) ethylenediamine) ligands, and substituted derivatives thereof. In formulae (IIA) and (IIB), substituents X are preferably selected from the group consisting of chloro, bromo, trifluoromethyl and nitro. In formula (IIA) substituents Y are preferably selected from the group consisting of hydrogen and methyl. A preferred tetradentate ligand is N,N'-bis(5-nitro-salicylidene)-ethylenediamine. Other suitable ligands include N,N'-1,2-cyclohexylenebis(2-hydroxyacetophenonylideneimine), 1,2-diphenylethylene-bis (2-hydroxyacetophenonylideneimine) and 1,1'-binaphtalene-2,2'-diaminobis(2-hydroxy-acetophenonylideneimine), all being described in Molecules (2002) 7:511-516.

The at least penta-coordinated metal complex ($a_5$) according to this fifth species may be made by reacting a suitable tetradentate ligand (i) such as defined hereinabove with a preferably bimetallic complex of the desired metal, more preferably a homobimetallic complex wherein the desired metal is coordinated with a non-anionic ligand $L^7$ and at least one anionic ligand, such as $[RuCl_2(p\text{-cymene})]_2$, $[RuCl_2(COD)]_2$ or $[RuCl_2(NBD)]_2$, wherein COD and NBD respectively mean cyclooctadiene and norbornadiene.

When the reaction product of this invention is produced by modifying a multi-coordinated metal complex (a) with an activating metal or silicon compound (b) in the presence of a further reactant (c) being an organic acid or having the general formula RYH, the molar ratio between, on the one hand, the hydrogen halide resulting from the reaction of (b) and (c) and, on the other hand, said multicoordinated metal complex (a) is an important parameter in the practice of the invention. Contrary to the teaching of the prior art (U.S. Pat. No. 6,284,852), this ratio is not selected to perform ligand protonation (especially since another preferred feature of this invention is the absence of protonatable ligands in the multicoordinated metal complex), but is selected to achieve at least partial cleavage of a bond between the metal center of the multicoordinated metal complex (a) and at least one multidentate Schiff base ligand (i) of multicoordinated metal complex (a). Therefore it was found desirable to select high values for the said molar ratio, said high values resulting both from a molar ratio above 5:1 between the activating metal or silicon compound (b) and multicoordinated metal complex (a), and from a molar equivalent amount between the further reactant (c) being an organic acid or having the general formula RYH and said activating metal or silicon compound (b). Said molar ratio may be achieved step by step by progressively adding the reactant (c) to the multicoordinated metal complex (a) and the activating metal or silicon compound (b), optionally in the presence of a solvent system as previously mentioned, over the predetermined contact time. The addition rate of the reactant may be changed, depending upon the multidentate Schiff base ligand (i) and the selected temperature, according to routine experimentation.

The progress of reaction with the multicoordinated metal complex (a) may be followed by one or more standard analytical techniques such as but not limited to infrared spectroscopy, carbon nuclear magnetic resonance (NMR) and proton NMR. These techniques will also be helpful in the determination of the precise nature of the reaction product of the invention. This nature may also be confirmed, after separation of the reaction product from the reaction medium and after its purification by suitable techniques (such as but not limited to re-crystallisation), by obtaining an X-ray diffractogram of the reaction product crystalline powder. Careful examination shows that the reaction product of the invention comprises the product of at least partial cleavage of a bond between the metal center and a multidentate Schiff base ligand (i). The bond that is partially cleaved as a result of the reaction may be a covalent bond or a coordination bond; it may be the bond between the metal center and the nitrogen atom of the Schiff base imino group, or it may be the bond between the metal center and the heteroatom (oxygen, sulfur or selenium) of the Schiff base ligand, or both such bonds may be simultaneously at least partially cleaved. The present invention does not require the said cleavage to be complete, thus partial bond cleavage leading to a mixture of the starting multicoordinated metal complex and of one or more reaction products is also within the scope of the invention. Because, as disclosed hereinafter, the modification reaction of the invention may be performed in situ in the presence of organic molecules or monomers such as unsaturated compounds (e.g. olefins, diolefins or alkynes) to be processed by the catalytic activity of the resulting reaction product, it is not essential that said reaction product may be isolated in the form of one single pure chemical entity.

In yet another aspect, the present invention also provides a supported catalyst, preferably for use in a heterogeneous catalytic reaction, comprising:
(A) a catalytic system comprising a catalytically active reaction product of:
(a) a multi-coordinated metal complex, a salt, a solvate or an enantiomer thereof, said multi-coordinated metal complex comprising (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) one or more other ligands, and
(b) an activating metal or silicon compound selected from the group consisting of:
copper (I) halides,
zinc compounds represented by the formula $Zn(R_5)_2$, wherein $R_5$ is halogen, $C_{1-7}$ alkyl or aryl,
aluminum compounds represented by the formula $AlR_6R_7R_8$ wherein each of $R_6$, $R_7$ and $R_8$ is independently selected from the group consisting of halogen and $C_{1-7}$ alkyl,
tin compounds represented by the formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl, and
silicon compounds represented by the formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl, and
(c) optionally a further reactant being an organic acid (such as defined hereinabove) or having the formula RYH, wherein Y is selected from the group consisting of oxygen, sulfur and selenium, and R is selected from the group consisting of hydrogen, aryl, heteocyclic, heterocyclic-substituted alkyl, arylalkyl and $C_{1-7}$ alkyl, and
(B) a supporting amount of a carrier suitable for supporting said catalytic system (a).

The catalytic system (A) included in the supported catalyst of this aspect of the invention may, in addition to the above-described reaction product, comprise one or more other catalytic species being known to the skilled person to exhibit catalytic activity in the reaction, for instance the metathesis reaction of an unsaturated compound, to be promoted. Such optional one or more other catalytic species should not be capable of negatively interfering with the components of the reaction product of the invention during the formation of said reaction product. For instance they should not be capable of desactivating the metal or silicon compound (b) and/or the optional further reactant (c).

In such a supported catalyst, said carrier (B) may be selected from the group consisting of porous inorganic solids (including silica, zirconia and alumino-silica), such as amorphous or paracrystalline materials, crystalline molecular sieves and modified layered materials including one or more inorganic oxides, and organic polymer resins such as polystyrene resins and derivatives thereof.

Porous inorganic solids that may be used as carriers (B) for the supported catalysts of the invention preferably have an open microstructure that allows molecules access to the relatively large surface areas of these materials, thereby enhancing their catalytic and/or sorptive activity. These porous materials can be sorted into three broad categories using the details of their microstructure as a basis for classification. These categories are the amorphous and paracrystalline supports, the crystalline molecular sieves and modified layered materials. The detailed differences in the microstructures of these materials manifest themselves in the catalytic and/or sorptive behavior of the materials, as well as in differences in various observable properties used to characterize them, such as their surface area, pore sizes, and pore size distribution, the presence or absence of X-ray diffraction patterns and the details in such patterns, and the appearance of the material microstructure when observed by transmission electron microscopy and/or electron diffraction methods. Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100-250 Angstrom particles of dense amorphous silica (Kirk-Othmer Encyclopedia of Chemical Technology, 3rd. ed., vol. 20, 766-781 (1982)), with the porosity resulting from voids between the particles.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum", Technical Paper No 19 Revised, Alcoa Research Laboratories, 54-59 (1987)). Since, in the case of either material, there is no long range order controlling the sizes of pores in the material, the variability in pore size is typically quite high. The sizes of pores in these materials fall into a regime called the mesoporous range, including (for example) pores within the range of about 1.5 to about 20 nm.

In sharp contrast to these structurally ill-defined solids, there are materials whose very narrow pore size distribution is controlled by the precisely repeating crystalline nature of the material's microstructure. These materials are usually called "molecular sieves", the most important examples of which are zeolites. Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since their pore dimensions are such as to accept for adsorption molecules of certain dimensions while rejecting those of larger dimensions, these materials are known as "molecular sieves" and are used in various ways to take advantage of this property. Such molecular sieves, both natural and synthetic, include a wide variety of positive ion-containing crystalline silicates. These silicates can be described as a rigid three-dimensional framework of $SiO_4$ and a Periodic Table Group IIIB element oxide, e.g., $AlO_4$, in which the tetrahedra are crosslinked by the sharing of oxygen atoms whereby the ratio of the total Group IIIB element, e.g., aluminum, and Group IVB element, e.g., silicon, atoms to oxygen atoms is 1:2. The electrovalence of the tetrahedra containing the Group IIIB element, e.g., aluminum, is balanced by the inclusion in the crystal of a cation, for example, an alkali metal or an alkaline earth metal cation. This can be expressed wherein the ratio of the Group IIIB element, e.g., aluminum, to the number of various cations, such as Ca, Sr, Na, K or Li, is equal to 1. One type of cation may be exchanged either entirely or partially with another type of cation by using ion exchange techniques in a conventional manner. By means of such cation exchange, it has been possible to modify the properties of a given silicate by suitable selection of the cation. Many of these zeolites have come to be designated by letter or other convenient symbols, as illustrated by zeolites A (U.S. Pat. No. 2,882, 243); X (U.S. Pat. No. 2,882,244); Y (U.S. Pat. No. 3,130, 007); ZK-5 (U.S. Pat. No. 3,247,195); ZK-4 (U.S. Pat. No. 3,314,752); ZSM-5 (U.S. Pat. No. 3,702,886); ZSM-11 (U.S. Pat. No. 3,709,979); ZSM-12 (U.S. Pat. No. 3,832,449); ZSM-20 (U.S. Pat. No. 3,972,983); ZSM-35 (U.S. Pat. No. 4,016,245); ZSM-23 (U.S. Pat. No. 4,076,842); MCM-22 (U.S. Pat. No. 4,954,325); MCM-35 (U.S. Pat. No. 4,981, 663); MCM-49 (U.S. Pat. No. 5,236,575); and PSH-3 (U.S. Pat. No. 4,439,409). The latter refers to a crystalline molecular sieve composition of matter made from a reaction mixture containing hexamethyleneimine, an organic compound which acts as directing agent for synthesis of a layered MCM-56. A similar composition, but with additional structural components, has been disclosed in EP-A-293,032. Hexamethylene-imine is also taught for making the crystalline molecular sieves MCM-22, MCM-35, MCM-49, and ZSM-12 (U.S. Pat. No. 5,021,141). A molecular sieve composition SSZ-25 is taught in U.S. Pat. No. 4,826,667 and EP-A-231,860, said zeolite being synthesized from a reaction mixture containing an adamantane quaternary ammonium ion. Molecular sieve material being selected from the group consisting of zeolites REY, USY, REUSY, dealuminated Y, ultrahydrophobic Y, silicon-enriched dealuminated Y, ZSM-20, Beta, L, silicoa-luminophosphates SAPO-5, SAPO-37, SAPO-40 and MCM-9, metalloalumino-phosphate MAPO-36, aluminophosphate VPI-5 and mesoporous crystalline MCM-41 are also suitable for including as a carrier (B) into a supported catalyst of this invention.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006. Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials. Other patents teaching pillaring of layered materials and the pillared products include U.S. Pat. Nos. 4,216,188; 4,248,739; 4,176,090; and 4,367,163; and European Patent Application 205,711. The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, at a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

In yet another aspect, the present invention provides a method of performing a meta-thesis reaction of an unsaturated compound in the presence of a catalytic component, wherein said catalytic component comprises a catalytically active reaction product of:

(a) a multi-coordinated metal complex, a salt, a solvate or an enantiomer thereof, said multi-coordinated metal complex comprising (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) one or more other ligands, and (b) an activating metal or silicon compound selected from the group consisting of copper (I) halides; zinc compounds represented by the formula $Zn(R_5)_2$, wherein $R_5$ is halogen, $C_{1-7}$ alkyl or aryl; aluminum compounds represented by the formula $AlR_6R_7R_8$ wherein each of $R_6$, $R_7$ and $R_8$ is independently selected from the group consisting of halogen and $C_{1-7}$ alkyl; tin compounds represented by the formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl; and silicon compounds represented by the formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl, and (c) optionally a further reactant being an organic acid (as defined hereinabove) or having the formula RYH, wherein Y is selected from the group consisting of oxygen, sulfur and selenium, and R is selected from the group consisting of hydrogen, aryl, heterocyclic, heterocyclic-substituted alkyl, arylalkyl and $C_{1-7}$ alkyl.

The metathesis reaction of an unsaturated compound according to this aspect of the invention may be olefin metathesis (the latter being as explained in the background of the invention or as defined in http://www.ilpi.com/organomet/olmetathesis.html), in particular the ring-opening metathesis polymerisation of cyclic olefins, or acetylenic metathesis (the latter being as defined in http://www.ilpi.com/organomet/acmetathesis.html, a reaction in which all carbon-carbon triple bonds in a mixture of alkynes are cut and then rearranged in a statistical fashion, and involving a metalla-cyclobutadiene intermediate).

The metathesis reaction of an unsaturated compound according to this aspect of the invention may be conducted in a continuous, semi-continuous, or batch manner and may involve a liquid and/or gas recycling operation as desired. The manner or order of addition of the reactants, catalyst, and solvent are usually not critical, but a few preferred embodiments will be described hereinafter. In particular, the metathesis reaction may be carried out in a liquid reaction medium that contains a solvent for the active catalyst, preferably one in which the reactants, including catalyst, are substantially soluble at the reaction temperature.

In a first embodiment of this aspect of the invention, the metathesis reaction is an olefin metathesis reaction for transforming a first olefin into at least one second olefin or into a linear olefin oligomer or polymer or into a cyclo-olefin. The invention thus relates to a method for performing an olefin metathesis reaction comprising contacting at least one first olefin with the catalytic component, optionally supported on a suitable carrier such as decribed hereinabove with reference to one previous aspect of the invention. The high activity of the metal complexes of this invention cause these compounds to coordinate with, and catalyze metathesis reactions between, many types of olefins. Exemplary olefin metathesis reactions enabled by the metal complexes of the present invention include, but are not limited to, RCM of acyclic dienes, cross metathesis reactions, de-polymerization of olefinic polymers and, more preferaby, ROMP of strained cyclic olefins. In particular, the catalytic components of this invention may catalyze ROMP of unsubstituted, mono-substituted and disubstituted strained mono-, bi- and polycyclic olefins with a ring size of at least 3, preferably 3 to 5, atoms; examples thereof include norbornene, cyclobutene, norbornadiene, cyclopentene, dicyclopentadiene, cycloheptene, cyclooctene, 7-oxanorbornene, 7-oxanorbornadiene, cyclooctadiene, cyclododecene, mono- and disubstituted derivatives thereof, especially derivatives wherein the substituent may be $C_{1-7}$ alkyl, cyano, diphenylphosphine, trimethylsilyl, methylaminomethyl, carboxylic acid or ester, trifluoromethyl, maleic ester, maleimido and the like, such as disclosed in U.S. Pat. No. 6,235,856, the content of which is incorporated herein in its entirety. The invention also contemplates ROMP of mixtures of two or more such monomers in any proportions. Further examples include water-soluble cyclic olefins such as exo-N-(N',N',N'-trimethylammonio) ethyl-bicyclo[2.2.1]hept-5-ene-2,3-dicarboximide chloride or exo-N-(N',N',N'-trimethylammonio)ethyl-bicyclo-7-oxabicyclo[2.2.1]hept-5-ene-2,3-dicarboximide chloride. As is well known to the skilled person, olefins such as cyclohexenes which have little or no ring strain cannot be polymerized because there is no thermodynamic preference for polymer versus monomer.

A ROMP reaction according to the invention may be carried out in an inert atmosphere for instance by dissolving a catalytic amount of the catalytic component in a suitable solvent and then adding one or more of the said strained cyclic olefins, optionally dissolved in the same or another solvent, to the catalyst solution, preferably under agitation. Because a ROMP system is typically a living polymerisation process, two or more different strained cyclic olefins may be polymerised in subsequent steps for making diblock and triblock copolymers, thus permitting to tailor the properties of the resulting material, provided that the ratio of chain initiation and chain propagation is suitably selected. Solvents that may be used for performing ROMP include all kinds of organic solvents such as protic solvents, polar aprotic solvents and non-polar solvents, as well as supercritical solvents such as carbon dioxide (while performing ROMP under supercritical conditions), which are inert with respect to the strained cyclic olefin and the catalytic component under the polymerization conditions used. More specific examples of suitable organic solvents include, but are not limited to, ethers (e.g. dibutyl ether, tetrahydrofuran, dioxane, ethylene glycol monomethyl or dimethyl ether, ethylene glycol monoethyl or diethyl ether, diethylene glycol diethyl ether or triethylene glycol dimethyl ether), halogenated hydrocarbons (e.g. methylene chloride, chloroform, 1,2-dichloroethane, 1,1,1-trichloroethane or 1,1,2,2-tetrachloroethane), carboxylic acid esters and lactones (e.g. ethyl acetate, methyl propionate, ethyl benzoate, 2-methoxyethyl acetate, γ-butyrolactone, δ-valerolactone or pivalolactone), carboxylic acid amides and lactams (e.g. N,N-dimethylformamide, N,N-diethylformamide, N,N-dimethylacetamide, tetramethylurea, hexamethyl-phosphoric acid triamide, γ-butyrolactam, ε-caprolactam, N-methyl-pyrrolidone, N-acetylpyrrolidone or N-methylcaprolactam), sulfoxides (e.g. dimethyl sulfoxide), sulfones (e.g. dimethyl sulfone, diethyl sulfone, trimethylene sulfone or tetramethylene sulfone), aliphatic and aromatic hydrocarbons (e.g. petroleum ether, pentane, hexane, cyclohexane, methylcyclohexane, benzene, chlorobenzene, o-dichlorobenzene, 1,2,4-trichlorobenzene, nitrobenzene, toluene or xylene), and nitriles (e.g. acetonitrile, propionitrile, benzonitrile or phenylacetonitrile).

The solubility of the polymer formed by ROMP will depend upon the choice of the strained cyclic olefin, the choice of the solvent and the molecular weight and concentration of the polymer obtained. When the strained cyclic olefin is polyunsaturated (e.g. dicyclopentadiene or norbornadiene), the polymer obtained may often be insoluble, whatever the solvent used. Polymerisation temperatures may range from about 0° C. to about 120° C., preferably 20° C. to 85° C., also depending upon the strained cyclic olefin and the solvent. The duration of polymerisation may be at least about 30 seconds, preferably at least about 1 minute, more preferably at least about 4 minutes, for instance about 30 minutes; the duration of polymerisation may be at most about 24 hours (although longer times may be used at the expense of economic conditions), preferably at most about 4 hours, and more preferably at most about 2 hours. The molar ratio of the strained cyclic olefin to the metal of the catalytic component of the invention is not critical and, depending upon the strained cyclic olefin to be polymerised, the selected temperature and the selected duration of polymerisation, may be at least about 100, preferably at least 250, more preferably at least 500. The said molar ratio is usually, i.e. for most strained cyclic olefins, at most about 5,000,000, preferably at most 500,000 and more preferably at most 200,000 in order to achieve optimal conversion within the above recommended duration of polymerisation. Before the polymer formed solidifies in the reactor or mold or, at will, when a desired molecular weight of the polymer has been achieved (as may be controlled for instance by monitoring reactor temperature and/or reaction mixture viscosity), an oxidation inhibitor and/or a terminating or chain-transfer agent may be added to the reaction mixture, if needed. The choice of the terminating or chain-transfer agent used is not critical to this invention, provided that the said terminating agent reacts with the catalytic component and produces another species which is inactive, i.e. not able to further propagate the polymerisation reaction, under the prevailing conditions (e.g. temperature). For instance, adding a molar excess (with respect to the catalytic component) of a carbonyl compound to the reaction mixture is able to produced a metal oxo and an olefin (or polymer) capped with the former carbonyl functionality; the cleaved polymer can then be separated from the catalyst by precipitation with methanol. Another way of cleaving the polymer from the catalyst may be by the addition of a vinylalkylether. Alternatively, reaction with several equivalents of a chain-transfer agent such as a diene is another way of cleaving the polymer chain, which method does not deactivate the catalytic component, permitting additional monomer to be polymerised, however possibly at the risk of broadening molecular weight distribution.

Because the metal complexes of this invention are stable in the presence of various functional groups, they may be used to catalyze metathesis of a wide variety of olefins under a wide variety of process conditions. In particular the olefinic compound to be converted by a metathesis reaction may include one or more, preferably at most two, functional atoms or groups, being for instance selected from the group consisting of ketone, aldehyde, ester (carboxylate), thioester, cyano, cyanato, epoxy, silyl, silyloxy, silanyl, siloxazanyl, boronato, boryl, stannyl, disulfide, carbonate, imine, carboxyl, amine, amide, carboxyl, isocyanate, thioisocyanate, carbodiimide, ether (preferably $C_{1-20}$ alkoxy or aryloxy), thioether (preferably $C_{1-20}$ thioalkoxy or thioaryloxy), nitro, nitroso, halogen (preferably chloro), ammonium, phosphonate, phosphoryl, phosphino, phosphanyl, $C_{1-20}$ alkylsulfanyl, arylsulfanyl, $C_{1-20}$ alkylsulfonyl, arylsulfonyl, $C_{1-20}$ alkylsulfinyl, arylsulfinyl, sulfonamido and sulfonate (preferably toluenesulfonate, methanesulfonate or trifluoromethanesulfonate). The said olefin functional atom or group may be either part of a substituting group of the olefin or part of the carbon chain of the olefin.

The metal complexes of this invention are also useful components for catalyzing, at relatively low temperatures (from about 20° C. to 80° C.), in the presence or absence of a solvent, the ring-closing metathesis of acyclic dienes such as, for instance, diallylic compounds (diallyl ether, diallyl thioether, diallyl phtalate, diallylamino compounds such as diallylamine, diallylamino phosphonates, diallyl glycine esters), 1,7-octadiene, substituted 1,6-heptadienes and the like.

The metal complexes of this invention may also be used as catalytic components for the preparation of telechelic polymers, i.e. macromolecules with one or more reactive end-groups which are useful materials for chain extension processes, block copolymer synthesis, reaction injection moulding, and polymer network formation. An example thereof is hydroxyl-telechelic polybutadiene which may be obtained from 1,5-cycooctadiene, 1,4-diacetoxy-cis-2-butene and vinyl acetate. For most applications, a highly functionalized polymer, i.e. a polymer with at least two functional groups per chain, is required. The reaction scheme for a telechelic polymer synthesis via ring opening metathesis polymerisation is well known to those skilled in the art: in such a scheme, acyclic olefins act as chain-transfer agents in order to regulate the molecular weight of the telechelic polymer produced. When $\alpha,\omega$-bifunctional olefins are used as chain-transfer agents, truly bi-functional telechelic polymers can be synthesized.

According to this aspect of the invention, olefin coupling may be performed by cross-metathesis comprising the step of contacting a first olefinic compound with the above-described catalytically active reaction product in the presence of a second olefin or functionalized olefin. The said first olefinic compound may be a diolefin or a cyclic mono-olefin with a ring size of at least 3 atoms, and the said metathesis cross-coupling is preferably performed under conditions suitable for transforming said cyclic mono-olefin into a linear olefin oligomer or polymer, or said diolefin into a mixture of a cyclic mono-olefin and an aliphatic alpha-olefin.

Depending upon the selection of the starting substrates for the olefin metathesis reaction and the desired organic molecule to be produced, the olefin metathesis reaction can yield a very wide range of end-products including biologically active compounds. For instance the reaction may be for transforming a mixture of two dissimilar olefins, at least one of which is an alpha-olefin, selected from (i) cyclodienes containing from 5 to 12 carbon atoms and (ii) olefins having the formula:

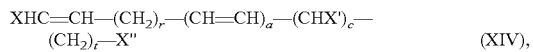
$$\text{XHC}=\text{CH}-(\text{CH}_2)_r-(\text{CH}=\text{CH})_a-(\text{CHX'})_c-(\text{CH}_2)_t-\text{X''} \quad (XIV),$$

into an unsaturated biologically active compound having the formula:

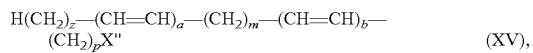
$$\text{H}(\text{CH}_2)_z-(\text{CH}=\text{CH})_a-(\text{CH}_2)_m-(\text{CH}=\text{CH})_b-(\text{CH}_2)_p\text{X''} \quad (XV),$$

wherein a is an integer from 0 to 2; b is selected from 1 and 2; c is selected from 0 and 1; m and p are such that the hydrocarbon chain in formula (V) contains from 10 to 18 carbon atoms; r and t are such that the combined total of carbon atoms in the hydrocarbon chains of the two dissimilar olefins of formula (XIV) is from 12 to 40; z is an integer from 1 to 10, and X, X' and X'' are atoms or groups each independently selected from hydrogen, halogen, methyl, acetyl, —CHO and —$OR_{12}$, wherein $R_{12}$ is selected from hydrogen and an alcohol protecting group selected from the group consisting of tetrahydropyranyl, tetrahydrofuranyl, tert-butyl, trityl, ethoxyethyl and $SiR_{13}R_{14}R_{15}$ wherein $R_{13}$, $R_{14}$ and $R_{15}$ are each independently selected from $C_{1-7}$ alkyl groups and aryl groups.

The said unsaturated biologically active compound having the formula (XV) may be a pheromone or pheromone precursor, an insecticide or a insecticide precursor, a pharmaceutically active compound or a pharmaceutical intermediate, a fragrance or a fragrance precursor. A few examples of the said unsaturated biologically active compounds include, but are not limited to, 1-chloro-5-decene, 8,10-dodecadienol, 3,8,10-dodecatrienol, 5-decenyl acetate, 11-tetradecenylacetate, 1,5,9-tetradeca-triene and 7,11-hexadecadienyl acetate. The latter is a pheronome commercially available under the trade name Gossyplure and is useful in pest control by effectively disrupting the mating and reproductive cycles of specifically targeted insect species, and which may be produced from 1,5,9-tetradecatriene, the latter being obtainable from cyclooctadiene and 1-hexene according to the present invention.

Ring-opening metathesis polymerization (ROMP) reactions using the catalytically active reaction product of the invention may proceed so quickly for olefinic monomers such as, but not limited to, dicyclopentadiene or oligomers thereof (i.e. Diels-Alder adducts formed with about 1 to 20 cyclopentadiene units), or mixtures thereof with strained monocyclic or polycyclic fused olefins (e.g. as defined in U.S. Pat. No. 6,235,856, the content of which is incorporated herein by reference), that polymerization control could become a problem in the absence of appropriate measures. This kind of problem is likely to occur during the molding of thermoset polymers wherein a liquid olefin monomer and a catalytic system are mixed and poured, cast or injected into a mold and wherein on completion of polymerization (i.e. "curing" of the article) the molded part is removed from the mold before any post cure processing that may be required, such as in the Reaction Injection Molding (hereinafter referred as "RIM") technique. It is well known that the ability to control reaction rates, i.e. the pot life of the reaction mixture, becomes more important in the molding of larger parts using this technique. When using the catalytically active reaction products of this invention, extending the pot life of the reaction mixture and/or controlling the rate of olefin metathesis polymerisation reaction may be effected in different ways, such as increasing the catalyst/olefin ratio and/or adding a polymerization retardant to the reaction mixture and/or selecting a particular mode of introduction of the olefin and the components of the catalytically active reaction product into the reactor (e.g. the mold). For instance, when the catalytically active reaction product of the invention results from modification of the multicoordinated metal complex by an activating metal or silicon compound alone (i.e. in the absence of a further reactant having the general formula RYH), rate control of the polymerisation reaction can be achieved by an improved embodiment comprising:

(a) a first step of contacting the optionally supported catalytic component of the invention with the olefin to be polymerised by ring-opening metathesis polymerization in a reactor at a first temperature at which said optionally supported catalytic component is substantially unreactive (inactive), and (b) a second heat activation step of bringing the reactor temperature (e.g. heating the contents of said reactor) up to a second temperature above the said first temperature, at which said optionally supported catalytic component is active, until completion of polymerisation.

In a more specific version of this improved embodiment, heat activation occurs in bursts rather than continuously, e.g. by repeating the sequence of steps (a) and (b).

Within the said controlled polymerization method, it should be understood that the non-reactivity of the catalytic component in the first step depends not only upon the first temperature but also upon the nature of the olefin(s) used in said molding process (e.g. RIM technique) and/or upon the olefin/catalytic component ratio. Preferably the first temperature is about 20° C. but, for specific olefins or specific olefin/catalytic component ratios, it may even be suitable to cool the reaction mixture below room temperature, e.g. down to about 0° C. The second temperature is preferably above 40° C. and may be up to about 90° C.

Alternatively, when the catalytically active reaction product of the invention results from modification of the multicoordinated metal complex by an activating metal or silicon compound in the presence of a further reactant (such as an organic acid or having the general formula RYH as decribed hereinabove), premature contact between said activating metal or silicon compound and said further reactant having the general formula RYH may result in premature formation of hydrogen halide which, if gaseous (e.g. hydrogen iodide, hydrogen bromide or hydrogen chloride respectively resulting from a metal or silicon compound including an iodine, bromine or chlorine atom), may escape from the reaction mixture or at least result in unknown concentrations, rate control of the metathesis reaction can be achieved by an improved embodiment wherein the unsaturated compound (e.g. olefin or alkyne) to be submitted to metathesis is distributed in at least two flows before introduction into the reactor, said at least two flows comprising:

a first flow comprising a first portion of said unsaturated compound in admixture with the multicoordinated metal complex and the reactant having the general formula RYH, and optionally a solvent, and a second flow comprising a second portion of said unsaturated compound in admixture with the activating metal or silicon compound, and optionally a solvent.

According to this improved embodiment of the process, the activating metal or silicon compound and the further reactant being an organic acid or having the general formula RYH may be kept separated until entrance into the reactor, thereby preventing premature formation of hydrogen halide. Also, since the multicoordinated metal complex and the reactant being an organic acid or having the general formula RYH are usually non-reactive versus each other, this improved embodiment of the process ensures that all amounts of the activating metal or silicon compound and of the further reactant being an organic acid or having the general formula RYH are available for reaction and, consequently, that all in situ formed hydrogen halide is available for chemical modification of the multicoordinated metal complex. Within this improved embodiment of the process, each of the first flow and the second flow may additionally comprise suitable additives and carriers, as long as such additives and carriers do not interfere with the critical components of each flow, e.g. by desactivating the metal or silicon compound included in the second flow and/or the further reactant being an organic acid or having the general formula RYH included in the first flow. According to this improved embodiment of the process, the number of flows before introduction into the reactor is not limited to two, for instance a third flow for a third portion of the unsaturated compound (e.g. olefin or alkyne) to be submitted to metathesis, optionally together with the further reactant being an organic acid or having the general formula RYH and optionally with a solvent but without the multicoordinated metal complex, may also be present. According to this improved embodiment of the process, the respective proportions of the first flow, the second flow, and optionally the third flow, are not particularly restricted, as long as the recommended molar ratios between the activating metal or silicon compound, the further reactant being an organic acid or having the general formula RYH, the multicoordinated metal complex and unsaturated compound (e.g. olefin or alkyne) to be submitted to metathesis are met and, preferably, as long as the solubility of each component of the catalytic system into said unsaturated compound is also met.

ROMP using the catalytic components of this invention readily achieve linear or crosslinked polymers of the abovementioned strained cyclic olefins, such as polynorbornenes and polydicyclopentadienes, with well controlled characteristics, i.e. average molecular weight and molecular weight distribution (polydispersity).

Polymerisation, in particular when performed in a mold such as in the RIM technique, may also occur in the presence of one or more formulation auxiliaries, such as antistatics, antioxidants, ceramics, light stabilizers, plasticizers, dyes, pigments, fillers, reinforcing fibers, lubricants, adhesion promoters, viscosity-enhancing agents and demolding agents, all said auxilaries being well known in the art.

Depending upon the specific reaction involved in this aspect of this invention, and especially when the said reaction is ROMP of strained cyclic olefins, reaction may also advantageously be performed under visible light or ultra-violet light irradiation, e.g. using a source of visible light or ultra-violet light being able to deliver sufficient energy to the reaction system.

The present invention will now be further explained by reference to the following set of examples which should be understood as merely illustrating various embodiments of the invention without limiting the scope thereof.

EXAMPLES 1-A TO 1-E

Preparation and Characterisation of Schiff Base Ligands

The following Schiff base ligands were prepared, purified and characterised as disclosed in WO 2005/035121:

N-(2,6-diisopropylphenyl)-2-hydroxy-3-tertbutyl-1-phenylmethaneimine (Schiff base 1-A) represented by the structural formula:

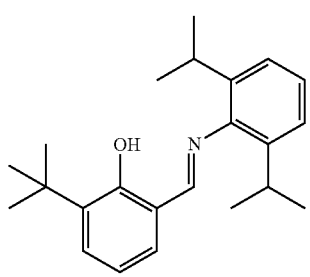

A

N-(4-bromo-2,6-dimethyl)-2-hydroxy-3-tertbutyl-1-phenylmethaneimine (Schiff base 1-B) represented by the structural formula:

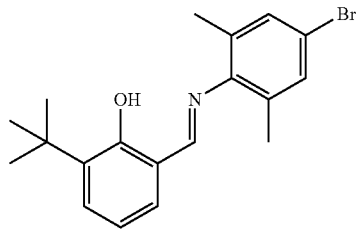

B

N-(4-bromo-2,6-dimethylphenyl)-2-hydroxy-1-phenyl-methaneimine (Schiff base 1-C) represented by the structural formula:

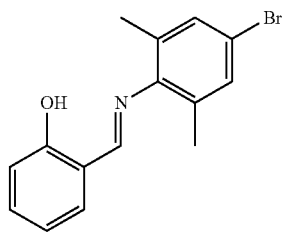

C

N-(4-bromo-2,6-dimethylphenyl)-2-hydroxy-4-nitro-1-phenylmethaneimine (Schiff base 1-D) represented by the structural formula:

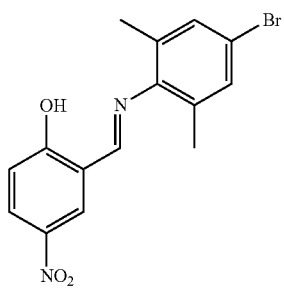

D

N-(2,6-diisopropylphenyl)-2-hydroxy-4-nitro-1-phenyl-methaneimine (Schiff base 1-E) represented by the structural formula:

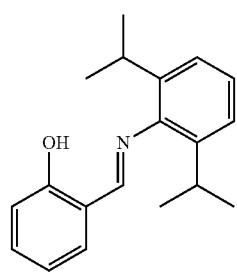

E

EXAMPLES 2 TO 8

Preparation and Characterisation of Schiff Base Substituted Ruthenium Complexes

The following ruthenium complexes coordinated with Schiff bases from examples 1-A to 1-E were prepared and characterised according to the procedure described in examples 2-8 of WO 2005/035121:

example 2 (obtained from Schiff base 1-C and methyl-lithium) represented by the structural formula:

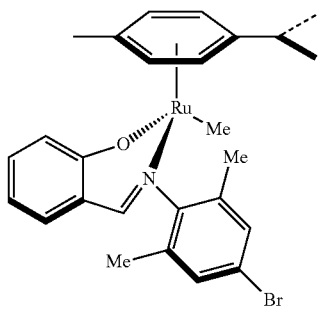

example 3 (obtained from Schiff base 1-E and methyl-lithium) represented by the structural formula:

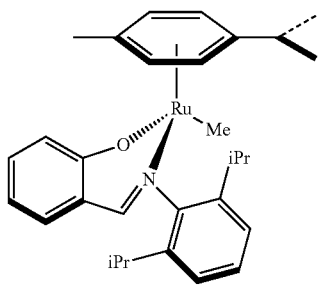

example 4 (obtained from Schiff base 1-B and methyl-lithium) represented by the structural formula:

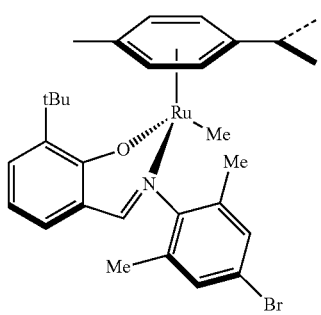

example 5 (obtained from Schiff base 1-A and phenylmagnesium chloride) represented by the structural formula:

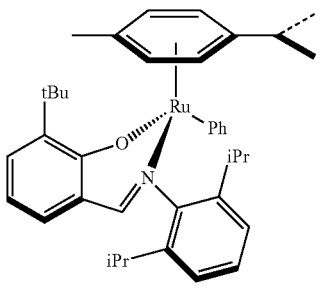

example 6 (obtained from Schiff base 1-A in the second step) represented by the structural formula:

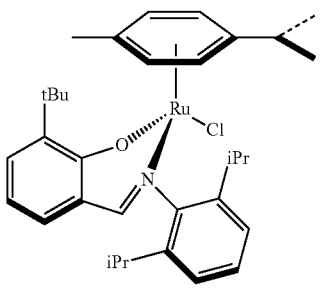

example 7 (obtained from Schiff base 1-A and methyllithium) represented by the structural formula:

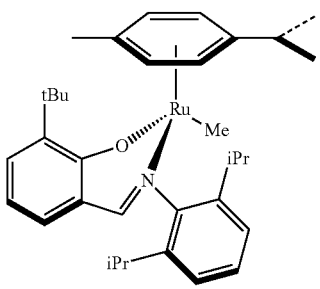

example 8 (obtained from Schiff base 1-A and pentafluorophenylmagnesium chloride) represented by the structural formula:

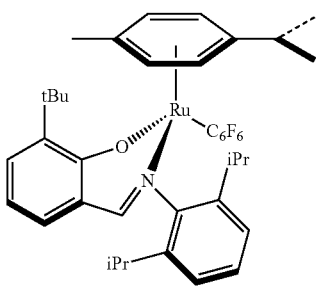

EXAMPLES 9 AND 10

Preparation and Characterisation of Bimetallic Schiff Base Substituted Ruthenium Complexes The two following bimetallic Schiff base substituted ruthenium complexes were made according to the procedure described in WO 2005/035121 (examples 9-10):

example 9 represented by the structural formula:

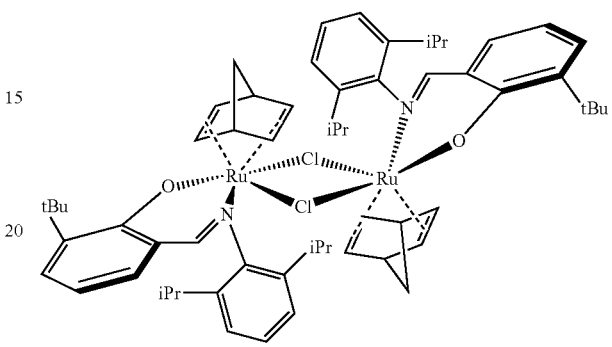

example 10 represented by the structural formula:

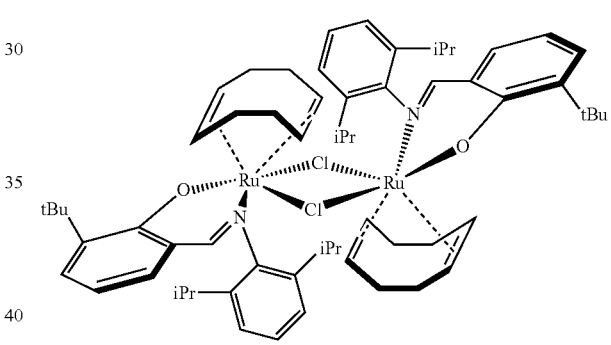

EXAMPLE 11

Manufacture of Multicoordinated Schiff Base Ruthenium Complexes

Figure 5:
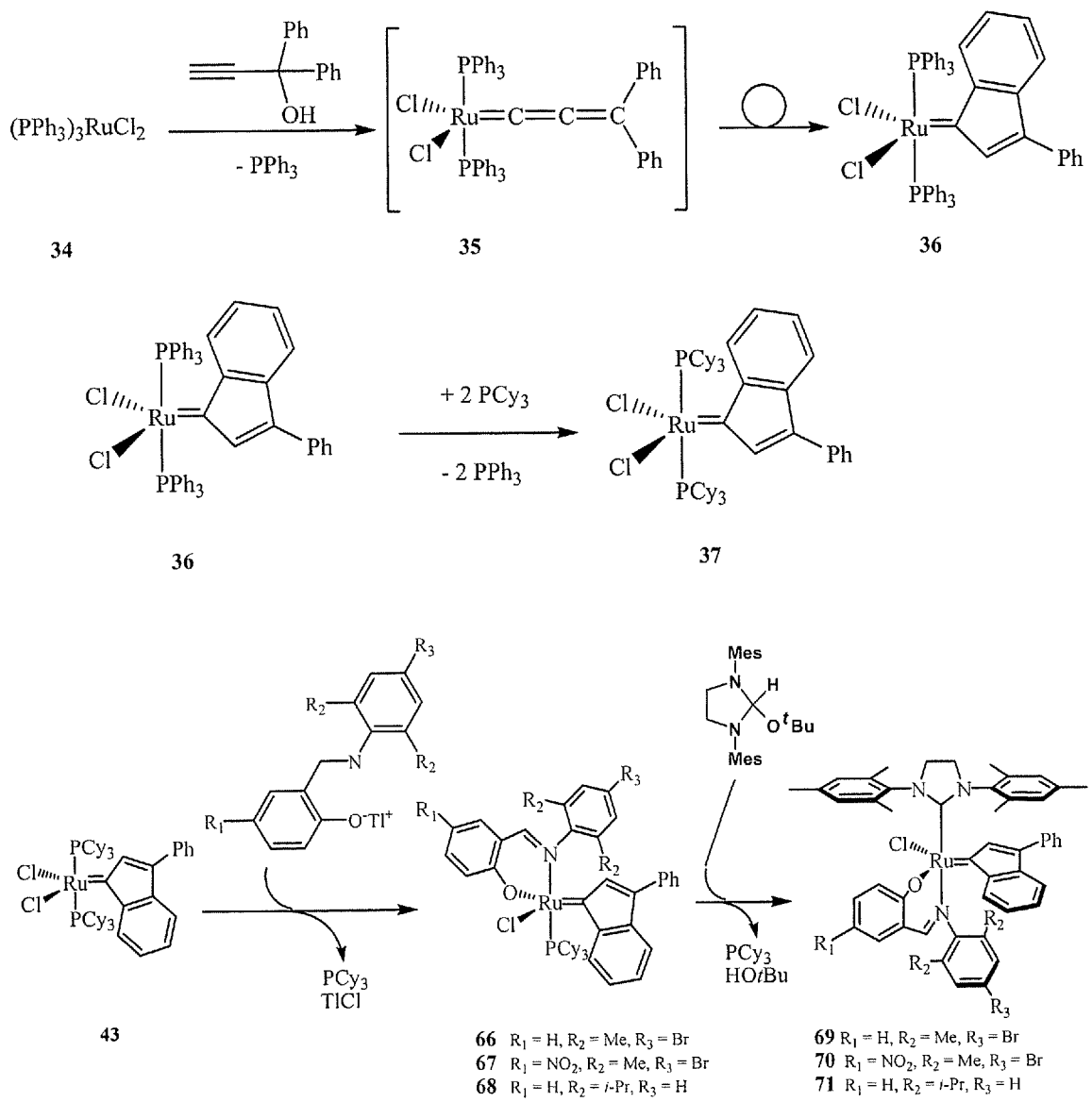
FIG. 5 shows a manufacturing scheme for a multicoordinated ruthenium complex suitable for modification according to the present invention.
Figure 6:
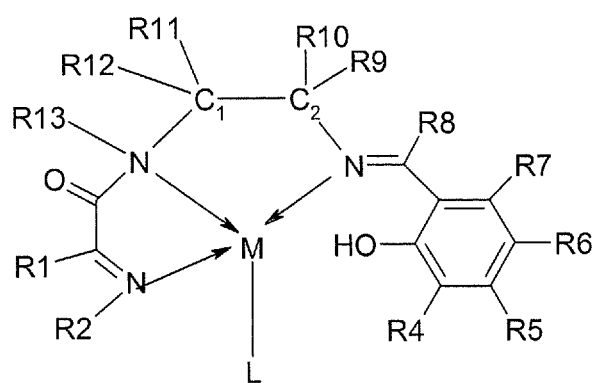
FIG. 6 shows monometallic complexes having the general formula (VA), derived from a tetradentate Schiff base ligand (IIIA), and the general formula (VB) suitable for modification according to the present invention
Figure 6:
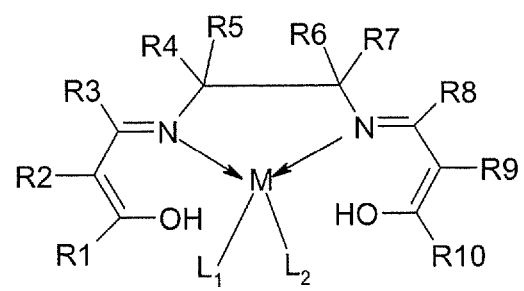

This example illustrates an alternative route of manufacture for the Schiff base substituted ruthenium complexes represented by formulae (VII.a) to (VII.f) in example 6 and FIG. 1 of WO 03/062253 (i.e. having a carbene ligand with a fused aromatic ring system having the formula (VI) shown in FIG. 3 of WO 03/062253). This alternative method is schematically shown in FIG. 5, wherein the following abbreviations are used:
Ph stands for phenyl,
Cy stands for cyclohexyl,
Me stands for methyl,
iPr stands for isopropyl, and
tBu stands for ter-butyl.

The scheme is self-understandable and shows a method which proceeds in five steps, starting from compound 34 and achieves, through intermediates 35, 36, 37 and 66-68, the desired Schiff base substituted ruthenium complexes 69-71 with better yields than the method disclosed in examples 1-6 and FIG. 1 of WO 03/062253.

EXAMPLE 12

Preparation and Characterisation of a Schiff-Base-Substituted Ruthenium Complex A Schiff base substituted ruthenium complex similar to the compound 70 shown in FIG. 5 (i.e. with $R_1$–$NO_2$, $R_2$=methyl and $R_3$=bromo), with the only exception that the carbene ligand with a fused aromatic ring system is replaced with a =$CHC_6H_5$ carbene ligand, was manufactured according to the procedure of example 11. This Schiff base substituted ruthenium complex may be represented by the general formula:

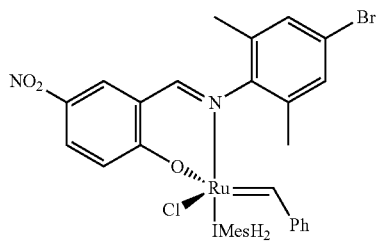

wherein $ImesH_2$ stands for dihydro-imidazol-2-ylidene and Ph stands for phenyl. This Schiff base substituted ruthenium complex was further characterised by means of proton nuclear magnetic resonance (hereinafter referred as NMR, performed at 300 MHz with $C_6D_6$ at 25° C.) and carbon NMR (performed at 75 MHz with $C_6D_6$) as follows:

$^1$H NMR ($CDCl_3$): δ 18.50 [1H, Ru=CHPh], 8.10 [d, 1H], 8.07 [d, 1H], 8.04 [d, 1H], 7.58 [s, 2H], 7.42-7.38 [m, 1H], 7.05 [s, 2H], 7.02 [s, 2H], 9.95 [s, 1H], 6.91 [s, 1H], 6.75 [s, 1H], 6.43 [1H], 6.36 [1H], 4.12-4.01 [m, 2H, $CH_2CH_2$], 2.57 [s, 3H, $CH_3$], 2.40 [s, 3H, $CH_3$], 2.29 [s, 3H, $CH_3$], 2.26 [s, 3H, $CH_3$], 2.13 [s, 3H, $CH_3$], 2.01 [s, 3H, $CH_3$], 1.48 [s, 3H, $CH_3$] and 1.03 [s, 3H, $CH_3$]; and $^{13}$C NMR ($CDCl_3$): δ 301.77 [Ru=C], 219.27 [NCN], 174.70 [C=N], 167.39 [C—O], 151.91, 150.13, 140.29-128.37, 123.99, 118.82, 118.03, 51.70 [$CH_2CH_2$], 51.08 [$CH_2CH_2$], and 21.24-17.80.

EXAMPLE 13

(Comparative)—Ring Opening Polymerisation of Cyclooctadiene Without Activation of a Schiff Base Ruthenium Complex Ring opening metathesis polymerisation of cyclooctadiene (beforehand dried over calcium hydride) was performed during 17 hours at 60° C. in tetrahydrofuran (THF) as a solvent, while using the Schiff base substituted ruthenium complex of example 12 as a catalyst in a molar ratio cyclooctadiene/catalyst equal to 500:1. A polymer having a number average molecular weight of 59,000 and a polydispersity of 1.4 was obtained in 96% yield.

EXAMPLE 14

Ring Opening Polymerisation of Cyclooctadiene with Activation of a Schiff Base Ruthenium Complex After charging an NMR-tube with the appropiate amount of the Schiff base substituted ruthenium complex of example 12 as a catalyst dissolved in deuterated toluene, there was added into the tube a mixture of:

cyclooctadiene (beforehand dried over calcium hydride) as the monomer, and a metal or silicon activator according to the invention.

The polymerization reaction was monitored as a function of time at 20° C. by integrating olefinic $^1$H signals of the formed polymer and the disappearing monomer. Various activators (aluminum trichloride being used as a solution in tetrahydrofuran) and various catalyst/monomerlactivator monomer ratios were tested during various periods of time, and the resulting monomer conversion was recorded in table 1.

TABLE 1

| Entry | Activator | catalyst/monomer/activator | Time (minutes) | Conversion (%) |
|---|---|---|---|---|
| 1 | $HSiCl_3$ | 1/30,000/70 | 30 | 93 |
|   |           |             | 60 | 100 |
| 2 | $HSiCl_3$ | 1/60,000/140 | 30 | 70 |
|   |           |              | 60 | 100 |
| 3 | $HSiCl_3$ | 1/90,000/140 | 15 | 49 |
|   |           |              | 30 | 79 |
|   |           |              | 60 | 100 |
| 4 | $HSiCl_3$ | 1/120,000/210 | 30 | 68 |
|   |           |               | 60 | 100 |
| 5 | $HSiCl_3$ | 1/150,000/210 | 30 | 86 |
|   |           |               | 60 | 100 |
| 6 | $HSiCl_3$ | 1/300,000/300 | 30 | 78 |
|   |           |               | 60 | 85 |
|   |           |               | 900 | 100 |
| 7 | $HSiCl_3$ | 1/3,000,000/1000 | 30 | 47 |
| 8 | $HSiCl_3$ | 1/90,000/140 | 30 | 89 |
|   |           |              | 60 | 100 |
| 9 | $HSiMe_2Cl$ | 1/30,000/70 | 30 | 50 |
|   |             |             | 60 | 55 |
| 10 | $SiMe_2Cl_2$ | 1/3,000/100 | 30 | 100 |
| 11 | $SiCl_4$ | 1/30,000/70 | 30 | 75 |
|    |          |             | 60 | 88 |
|    |          |             | 900 | 100 |
| 12 | $SnCl_4$ | 1/3,000/100 | 120 | 31 |
| 13 | CuCl | 1/3,000/100 | 120 | 63 |
|    |      |             | 900 | 100 |

EXAMPLE 15

(Comparative)—Ring Closing Metathesis of Diethyl Diallylmalonate Without Activation of a Schiff Base Ruthenium Complex An NMR-tube was charged with 0.6 mL of a catalyst solution in $CD_2Cl_2$ (4.52 mM or 0.002712 mmole of the Schiff base substituted ruthenium complex of example 12 as a catalyst). Next 200 molar equivalents (0.13 mL) of diethyl diallylmalonate was added and the NMR tube was closed. The progress of the ring closing reaction was monitored at 20° C. by integration of $^1$H signals of allylic protons of the reaction product and of the disappearing substrate. However no reaction product was obtained after 180 minutes under such conditions.

EXAMPLE 16

Ring Closing Metathesis of Diethyl Diallylmalonate with Activation of a Schiff Base Ruthenium Complex The procedure of example 15 was repeated, except that $HSiCl_3$ was diluted into diethyl diallylmalonate immediately prior to introduction into the NMR-tube, in such a way that the catalyst/substrate/$HSiCl_3$ ratio was 1/200/50. Under such conditions, conversion of diethyl diallylmalonate was 71% after 110 minutes, and 84% after 180 minutes.

EXAMPLE 17

Ring Opening Polymerisation of Dicyclopentadiene with Activation of a Schiff Base Ruthenium Complex This example illustrates an embodiment of a ROMP process with activation of the Schiff base substituted ruthenium complex obtained in example 12 (acting as the catalyst to be activated) by both a chlorinated silane ($CH_3Cl_2SiH$) and a phenol (2,6-di-tert-butyl-4-sec-butylphenol, commercially available from Schenectady International, Inc., Korea under the trade name ISONOX 132), wherein said silane activating compound and said phenol are kept separated until their entrance into the polymerisation reactor.

The operating procedure was as follows: in a first 14 ml glass vessel, 1 molar equivalent of the catalyst (dissolved in $CH_2Cl_2$) was mixed with 5 ml dicyclopentadiene (hereinafter referred as DCPD), 60 molar equivalents ISONOX 132, and optionally 0.15 g of an additive. Said additive was either short glass fibres (2 mm length) in order to reinforce the resulting polymer (entry 4 in table 2) or an organic pigment (type: aromatic alcohol) commercially available under the trade name Disney Magic Artist from the company BIC (Clichy, France) in order to impart color to the resulting polymer (entries 2-3 and 5 in table 2). The color of said pigment is specified in table 2 below for each relevant experiment. Another 14 ml glass vessel was filled with 5 ml DCPD, 22 µl vinylnorbornene (acting as a chain transfer agent) and 30 molar equivalents $CH_3Cl_2SiH$ (from a 10 mL solution of 800 µL $CH_3Cl_2SiH$ in $CH_2Cl_2$). The content of the second vessel was added to the first vessel and, at the moment of addition, time measurement was started. The total volume of DCPD (10 ml) corresponds to 30,000 molar equivalents of the monomer with respect to the catalyst.

Reaction was allowed to proceed for a certain time (expressed in minutes in table 2 below), after which temperature quickly decreases. The polymerisation reaction was extremely exothermic, possibly involving foaming of the mixture, and the maximum temperature $T_{max}$ (expressed in ° C. in table 2 below) was duly recorded by means of a thermocouple. In a few embodiments of this experimental set-up, dynamic mechanical analysis (hereinafter referred as DMA) was performed on the resulting polydicyclopentadiene in order to assess its glass transition temperature $T_g$. Results of DMA show that $T_{max}$ is in good accordance (statistically significantly) with $T_g$.

The following table 2 indicates the maximum temperature $T_{max}$ obtained while changing the type of additive.

TABLE 2

| entry | additive type | time [min.] | $T_{max}$ [° C.] |
|---|---|---|---|
| 1 | | 7.3 | 158 |
| 2 | orange | 6.4 | 176 |
| 3 | yellow | 4.3 | 189 |
| 4 | glass fibres | 8.2 | 164 |
| 5 | white | 6.1 | 172 |

The data presented in table 2 show that, under the above stated experimental conditions, polydicyclopentadiene with a glass transition temperature $T_g$ above 158° C. can reproducibly be obtained within about 4 to 9 minutes according to this invention, and that said high $T_g$ polymer may be reinforced or coloured at will. Without wishing to be bound by theory, it may be postulated that the $T_g$ increase observed for entries 2-3 and 5 with respect to that of entry 1 without additive may be due to the chemical constitution of the organic pigments which makes them able to act as a further reactant with the chlorinated silane activating compound.

EXAMPLE 18

Ring Opening Polymerisation of Dicyclopentadiene with Activation of a Schiff Base Ruthenium Complex The procedure of example 17 was repeated, except that 2,6-di-tert-butyl-4-sec-butylphenol was replaced with 3,5-dimethylphenol, i.e. a less sterically hindered phenol, and no additive was added in any experiment, and (only in the experimental entry 3 of table 3) the experimental scale was increased by bringing the total DCPD volume to 90 ml instead of 10 ml.

The following table 3 indicates the maximum temperature $T_{max}$ obtained while changing reaction parameters such as the type of silicon activating compound and/or its molar ratio with respect to the catalyst.

TABLE 3

| activator ratio [eq.] | activator type | time [min.] | $T_{max}$ [° C.] | entry |
|---|---|---|---|---|
| 30 | $CH_3SiHCl_2$ | 3.6 | 180 | 1 |
| 15 | $SiCl_4$ | 4.8 | 185 | 2 |
| 30 | $CH_3SiHCl_2$ | 4.0 | 203 | 3 |

The data presented in table 3 show that, under the above stated experimental conditions, polydicyclopentadiene with a glass transition temperature $T_g$ above 180° C. can reproducibly obtained within about 3 to 5 minutes according to this invention.

EXAMPLE 19

Schiff Base Ligands

The eight Schiff base ligands and nitro-ligands having the formulae shown in the following table 4 were prepared and purified according to the method described in example 1 of WO 2005/035121.

TABLE 4

| Ref. N° | ligand | nitro-ligand |
|---|---|---|
| 1 | 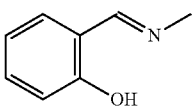 | 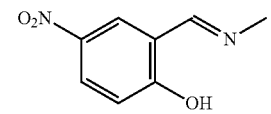 |
| 2 | 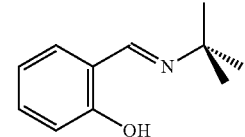 | 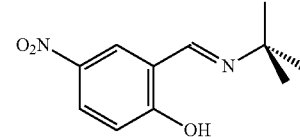 |
| 3 | 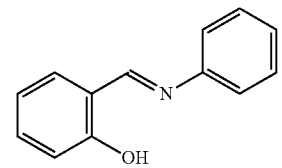 [SMILES: Oc1ccccc1/C=N/c1ccccc1] | 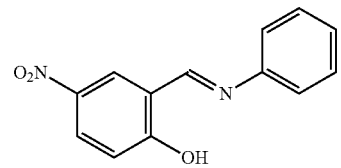 [SMILES: O=[N+]([O-])c1ccc(O)c(/C=N/c2ccccc2)c1] |
| 4 | 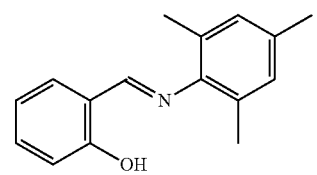 [SMILES: Cc1cc(C)c(/N=C/c2ccccc2O)c(C)c1] | 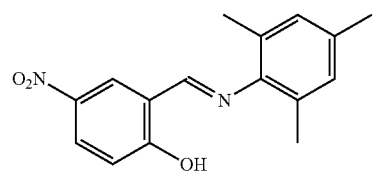 [SMILES: Cc1cc(C)c(/N=C/c2cc([N+](=O)[O-])ccc2O)c(C)c1] |

EXAMPLES 20 TO 27

Preparation of Monometallic Schiff Base Substituted Ruthenium Complexes

Monometallic ruthenium complexes each having one Schiff base ligand or nitro-ligand from example 19, and wherein ruthenium is also coordinated with a chloro atom and a p-cymene group, were prepared by performing the two first steps of the procedure described in examples 2-8. Each ruthenium complex was characterized by means of proton NMR performed with $CDCl_3$ at 25° C. as follows:

complex (example 20) obtained from the ligand 1 of example 19: δ at 8.35 (1H), 6.85-7.20 (4H), 3.12 (3H), 5.47 (2H), 5.34 (2H), 2.92 (1H), 2.17 (3H) and 1.25 (6H) ppm;

complex (example 21) obtained from the ligand 2 of example 19: δ at 8.25 (1H), 6.85-7.00 (4H), 2.54 (9H), 5.46 (2H), 5.32 (2H), 2.75 (1H), 2.24 (3H) and 1.25 (6H) ppm;

complex (example 22) obtained from the ligand 3 of example 19: δ at 7.76 (1H), 7.20-7.46 (4H), 6.92-7.02 (5H), 5.49 (2H), 5.34 (2H), 2.92 (1H), 2.16 (3H), and 1.25 (6H) ppm;

complex (example 23) obtained from the ligand 4 of example 19: δ at 9.25 (1H), 6.75 (2H), 2.19 (3H), 2.13 (6H), 6.80-7.60 (4H), 5.39 (2H), 5.46 (2H), 2.77 (1H), 2.16 (3H) and 1.29 (6H) ppm;

complex (example 24) obtained from the nitro-ligand 1 of example 19: δ at 8.00 (1H), 6.86-7.49 (3H), 3.12 (3H), 5.47 (2H), 5.34 (2H), 2.92 (1H), 2.17 (3H) and 1.25 (6H) ppm;

complex (example 25) obtained from the nitro-ligand 2 of example 19: δ at 8.10 (1H), 6.95-7.26 (3H), 2.54 (9H), 5.46 (2H), 5.32 (2H), 2.75 (1H), 2.24 (3H) and 1.25 (6H) ppm;

complex (example 26) obtained from the nitro-ligand 3 of example 19: δ at 8.06 (1H), 7.39-7.61 (3H), 6.92-6.96 (5H), 5.49 (2H), 5.34 (2H), 2.92 (1H), 2.16 (3H) and 1.25 (6H) ppm; and complex (example 27) obtained from the nitro-ligand 4 of example 19: δ at 8.80 (1H), 6.75 (2H), 2.19 (3H), 2.13 (6H), 6.85-7.50 (3H), 5.39 (2H), 5.46 (2H), 2.77 (1H), 2.16 (3H) and 1.29 (6H) ppm;

EXAMPLE 28

Activation of Schiff Base Substituted Ruthenium Complexes for the Ring-Opening Metathesis Polymerisation of Cyclooctadiene The monometallic Schiff base substituted ruthenium complexes of examples 2 to 8, the bimetallic Schiff base substituted ruthenium complexes of examples 9 and 10, and the monometallic Schiff base substituted ruthenium complexes of examples 20 to 27 are activated under the experimental conditions of example 14, i.e. with:

an activating agent such as copper (I) chloride, tin tetrachloride, or a chlorinated silicon compound such as $HSiCl_3$, $HSiMe_2Cl$, $SiMe_2Cl_2$ or $SiCl_4$ (wherein Me stands for methyl), and a molar ratio of said activating agent to said ruthenium complex ranging from 70 to 1,000.

The activated Schiff base substituted ruthenium complexes are then tested in the ring-opening metathesis polymerisation of cyclooctadiene under the experimental conditions of example 14, i.e. with a molar ratio of cyclooctadiene to ruthenium ranging from 3,000 to 3,000,000 and withion reaction times ranging from 15 to 900 minutes. Polymer conversions comparable to those mentioned in table 1 are obtained. Polymerisation proceeds within shorter reaction times and/or at lower reaction temperatures as compared to the starting non-activated ruthenium complex under the same conditions.

EXAMPLE 29

Activation of Schiff Base Substituted Ruthenium Complexes for the Ring-Opening Metathesis Polymerisation of Dicyclopentadiene The monometallic Schiff base substituted ruthenium complexes of examples 2 to 8, the bimetallic Schiff base substituted ruthenium complexes of examples 9 and 10, and the monometallic Schiff base substituted ruthenium complexes of examples 20 to 27 are activated in situ under the experimental conditions of example 17, i.e. with:
- $CH_3Cl_2SiH$ as the activating agent,
- ISONOX 132 as a reactive phenol,
- a molar ratio of said activating agent to ruthenium of 30:1, and
- a molar ratio of said reactive phenol to ruthenium of 60:1.

The activated Schiff base substituted ruthenium complexes formed in situ are tested in the ring-opening metathesis polymerisation of dicyclopentadiene under the experimental conditions of example 17, i.e. with a molar ratio of dicyclopentadiene to ruthenium of 30,000, and optionally in the additional presence of additives.

Under the above stated experimental conditions, polydicyclopentadiene with a glass transition temperature $T_g$ above 140° C. can reproducibly be obtained within about 4 to 12 minutes according to this embodiment of the invention.

EXAMPLE 30

Activation of Schiff Base Substituted Ruthenium Complexes for the Ring-Opening Metathesis Polymerisation of Dicyclopentadiene The monometallic Schiff base substituted ruthenium complexes of examples 2 to 8, the bimetallic Schiff base substituted ruthenium complexes of examples 9 and 10, and the monometallic Schiff base substituted ruthenium complexes of examples 20 to 27 are activated in situ under the experimental conditions of example 18, i.e. with:
- $CH_3Cl_2SiH$ or $SiCl_4$ as the activating agent,
- 3,5-dimethylphenol as a reactive phenol,
- a molar ratio of said activating agent to ruthenium ranging from 15:1 to 30:1, and
- a molar ratio of said reactive phenol to ruthenium of 60:1.

The activated Schiff base substituted ruthenium complexes formed in situ are tested in the ring-opening metathesis polymerisation of dicyclopentadiene under the experimental conditions of example 18, i.e. with a molar ratio of dicyclopentadiene to ruthenium of 30,000.

Under the above stated experimental conditions, polydicyclopentadiene with a glass transition temperature $T_g$ above 170° C. can reproducibly be obtained within about 3 to 10 minutes according to this embodiment of the invention.

EXAMPLE 31

(Comparative)—Ring Closing Metathesis of Diethyl Diallylmalonate without Activation of a Schiff Base Ruthenium Complex An NMR-tube was charged with a catalyst solution in $CD_2Cl_2$ (4.52 mM or 0.002712 mmole of the Schiff base substituted ruthenium complex of example 11 shown as complex 70 in FIG. 5 as a catalyst). Next 200 molar equivalents (0.13 mL) of diethyl diallylmalonate was added and the NMR tube was closed. The progress of the ring closing reaction was monitored at 30° C. by integration of $^1H$ signals of allylic protons of the reaction product and of the disappearing substrate. No reaction product was obtained after 275 minutes under such conditions.

EXAMPLE 32

Ring Closing Metathesis of Diethyl Diallylmalonate with Activation of a Schiff Base Ruthenium Complex The procedure of example 31 was repeated, except that $HSiCl_3$ was diluted into diethyl diallylmalonate immediately prior to introduction into the NMR-tube, in such a way that the catalyst/substrate/$HSiCl_3$ ratio was 1/200/50. Under such conditions, conversion of diethyl diallylmalonate was 32.6% after 90 minutes and 63.2% after 275 minutes.

EXAMPLE 33

Manufacture of a Pentacoordinated Schiff Base Ruthenium Complex

The procedure of example 11, as illustrated in FIG. 5, was repeated, except that in the last step the bis(mesityl)imidazolylidene reactant was replaced with the corresponding bis(2,6-dimethylphenyl)imidazolylidene reactant, thus forming the ruthenium complex having the structure below:

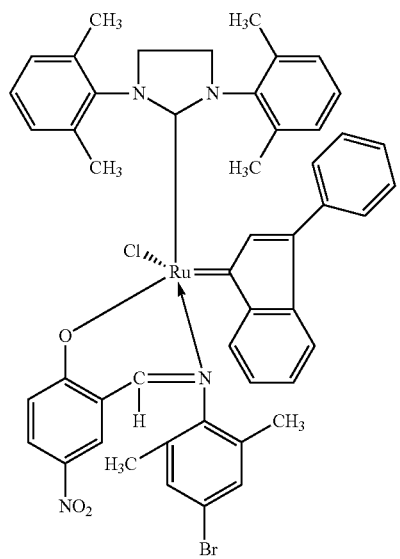

This Schiff base substituted ruthenium complex was further characterised by means of proton nuclear magnetic resonance (hereinafter referred as NMR, performed at 300 MHz with $C_6D_6$ at 25° C.) and carbon NMR (performed at 75 MHz with $C_6D_6$).

EXAMPLE 34

(Comparative)—Ring Closing Metathesis of Diethyl Diallylmalonate without Activation of a Schiff Base Ruthenium Complex An NMR-tube was charged with a catalyst solution in $CD_2Cl_2$ (4.52 mM or 0.002712 mmole of the Schiff base substituted ruthenium complex of example 33 as a catalyst).

Next 200 molar equivalents (0.13 mL) of diethyl diallylmalonate was added and the NMR tube was closed. The progress of the ring closing reaction was monitored at 22° C. by integration of $^1$H signals of allylic protons of the reaction product and of the disappearing substrate. No reaction product was obtained after 180 minutes under such conditions.

EXAMPLE 35

Ring Closing Metathesis of Diethyl Diallylmalonate with Activation of a Schiff Base Ruthenium Complex The procedure of example 34 was repeated, except that $HSiCl_3$ was diluted into diethyl diallylmalonate immediately prior to introduction into the NMR-tube, in such a way that the catalyst/substrate/$HSiCl_3$ ratio was 1/200/50. Under such conditions, conversion of diethyl diallylmalonate was 50.7% after 180 minutes.

EXAMPLE 36

Manufacture of a Pentacoordinated Schiff Base Ruthenium Complex

The procedure of example 11, as illustrated in FIG. 5, was repeated, except that:
- in the penultimate step, a thallium salt was used wherein $R_2$ is hydrogen and $R_3$ is tert-butyl, and
- in the last step the bis(mesityl)imidazolylidene reactant was replaced with the corresponding bis(2,6-dimethylphenyl)imidazolylidene reactant, thus forming the ruthenium complex having the structure below:

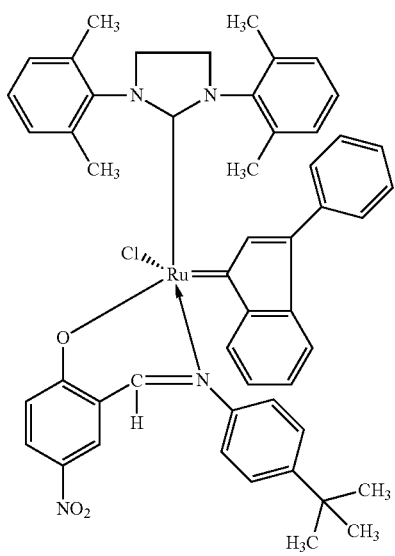

This Schiff base substituted ruthenium complex was further characterised by means of proton nuclear magnetic resonance (hereinafter referred as NMR, performed at 300 MHz with $C_6D_6$ at 25° C.) and carbon NMR (performed at 75 MHz with $C_6D_6$).

EXAMPLE 37

(Comparative)—Ring Closing Metathesis of Diethyl Diallylmalonate without Activation of a Schiff Base Ruthenium Complex An NMR-tube was charged with a catalyst solution in $CD_2Cl_2$ (4.52 mM or 0.002712 mmole of the Schiff base substituted ruthenium complex of example 36 as a catalyst). Next 200 molar equivalents (0.13 mL) of diethyl diallylmalonate was added and the NMR tube was closed. The progress of the ring closing reaction was monitored at 22° C. by integration of $^1$H signals of allylic protons of the reaction product and of the disappearing substrate. Conversion was 2% after 240 minutes under such conditions.

EXAMPLE 38

Ring Closing Metathesis of Diethyl Diallylmalonate with Activation of a Schiff Base Ruthenium Complex The procedure of example 37 was repeated, except that $HSiCl_3$ was diluted into diethyl diallylmalonate immediately prior to introduction into the NMR-tube, in such a way that the catalyst/substrate/$HSiCl_3$ ratio was 1/200/50. Under such conditions, conversion of diethyl diallylmalonate was 93.3% after 14 minutes and 100% after 37 minutes.

EXAMPLE 39

Manufacture of a Pentacoordinated Schiff Base Ruthenium Complex

The procedure of example 11, as illustrated in FIG. 5, was repeated, except that in the penultimate step, a thallium salt was used wherein $R_2$ is hydrogen and $R_3$ is tert-butyl, thus forming the ruthenium complex having the structure below:

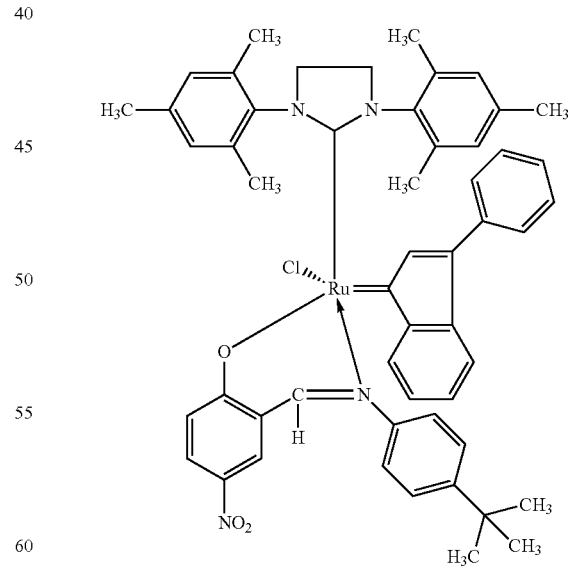

This Schiff base substituted ruthenium complex was further characterised by means of proton nuclear magnetic resonance (hereinafter referred as NMR, performed at 300 MHz with $C_6D_6$ at 25° C.) and carbon NMR (performed at 75 MHz with $C_6D_6$).

EXAMPLE 40

(Comparative)—Ring Closing Metathesis of Diethyl Diallylmalonate without Activation of a Schiff Base Ruthenium Complex An NMR-tube was charged with a catalyst solution in $CD_2Cl_2$ (4.52 mM or 0.002712 mmole of the Schiff base substituted ruthenium complex of example 39 as a catalyst). Next 200 molar equivalents (0.13 mL) of diethyl diallylmalonate was added and the NMR tube was closed. The progress of the ring closing reaction was monitored at 22° C. by integration of $^1H$ signals of allylic protons of the reaction product and of the disappearing substrate. Conversion was 2% after 240 minutes under such conditions.

EXAMPLE 41

Ring Closing Metathesis of Diethyl Diallylmalonate with Activation of a Schiff Base Ruthenium Complex The procedure of example 40 was repeated, except that $HSiCl_3$ was diluted into diethyl diallylmalonate immediately prior to introduction into the NMR-tube, in such a way that the catalyst/substrate/$HSiCl_3$ ratio was 1/200/50. Under such conditions, conversion of diethyl diallylmalonate was 92.7% after 14 minutes and 99.5% after 42 minutes.

EXAMPLE 42

(Comparative)—Ring Opening Polymerisation of Cyclooctadiene without Activation of a Schiff Base Ruthenium Complex Ring opening metathesis polymerisation of cyclooctadiene (beforehand dried over calcium hydride) was performed during 17 hours at 22° C. in 0.20 mL toluene as a solvent, while using 0.002712 millimole of the Schiff base substituted ruthenium complex of example 36 as a catalyst in a molar ratio cyclooctadiene/catalyst equal to 3,000:1. Checking conversion with NMR, no polymer was obtained after 17 hours.

EXAMPLE 43

Ring Opening Polymerisation of Cyclooctadiene with Activation of a Schiff Base Ruthenium Complex The procedure of example 42 was repeated, except that 0.0191 ml $HSiCl_3$ was added to the reaction mixture, thus achieving a catalyst/monomer/activator ratio of 1:3,000:70. Full monomer conversion was obtained after 1 minute.

EXAMPLE 44

(Comparative)—Ring Opening Polymerisation of Cyclooctadiene without Activation of a Schiff Base Ruthenium Complex Ring opening metathesis polymerisation of cyclooctadiene (beforehand dried over calcium hydride) was performed during 17 hours at 22° C. in 0.20 mL toluene as a solvent, while using 0.002712 millimole of the Schiff base substituted ruthenium complex of example 39 as a catalyst in a molar ratio cyclooctadiene/catalyst equal to 3,000:1. Checking conversion with NMR, no polymer was obtained after 17 hours.

EXAMPLE 45

Ring Opening Polymerisation of Cyclooctadiene with Activation of a Schiff Base Ruthenium Complex The procedure of example 44 was repeated, except that 0.0191 ml $HSiCl_3$ was added to the reaction mixture, thus achieving a catalyst/monomer/activator ratio of 1:3,000:70. Full monomer conversion was obtained after 1 minute.

EXAMPLE 46

(Comparative)—Ring Opening Polymerisation of Cyclooctadiene without Activation of a Schiff Base Ruthenium Complex Ring opening metathesis polymerisation of cyclooctadiene (beforehand dried over calcium hydride) was performed during 17 hours at 22° C. in 0.20 mL toluene as a solvent, while using 0.002712 millimole of the Schiff base substituted ruthenium complex of example 33 as a catalyst in a molar ratio cyclooctadiene/catalyst equal to 3,000:1.

EXAMPLE 47

Ring Opening Polymerisation of Cyclooctadiene with Activation of a Schiff Base Ruthenium Complex The procedure of example 46 was repeated, except that 0.0191 ml $HSiCl_3$ was added to the reaction mixture, thus achieving a catalyst/monomer/activator ratio of 1:3,000:70. Full monomer conversion was obtained after 9 hours.

EXAMPLE 48

(Comparative)—Ring Opening Polymerisation of Cyclooctadiene without Activation of a Schiff Base Ruthenium Complex Ring opening metathesis polymerisation of cyclooctadiene (beforehand dried over calcium hydride) was performed during 17 hours at 22° C. in 0.20 mL toluene as a solvent, while using 0.002712 millimole of the Schiff base substituted ruthenium complex of example 11 shown as complex 70 in FIG. 5 as a catalyst in a molar ratio cyclooctadiene/catalyst equal to 3,000:1.

EXAMPLE 49

Ring Opening Polymerisation of Cyclooctadiene with Activation of a Schiff Base Ruthenium Complex The procedure of example 48 was repeated, except that 0.0191 ml $HSiCl_3$ was added to the reaction mixture, thus achieving a catalyst/monomer/activator ratio of 1:3,000:70.91% monomer conversion was obtained after 320 minutes.

EXAMPLE 50

Ring Opening Polymerisation of Dicyclopentadiene with Activation of a Schiff Base Ruthenium Complex with a Silicon Compound This example illustrates an embodiment of a ROMP process with activation of the Schiff base substituted ruthenium complex obtained in example 39 (acting as the catalyst to be activated) by both $HSiCl_3$ and propanol. The procedure of example 17 was repeated with a catalyst/monomer/propanol/silane ratio equal to 1:30,000:90:30, and starting from room temperature (22° C.). Reaction was allowed to proceed for 105 seconds until temperature reached a maximum $T_{max}$=180° C., after which time temperature quickly decreases. This shows that, under these experimental conditions, polydicyclopentadiene with a glass transition temperature $T_g$ of about 180° C. can be obtained within about 2 minutes according to the present invention.

EXAMPLE 51

Ring Opening Polymerisation of Dicyclopentadiene with Activation of a Schiff Base Ruthenium Complex with a Silicon Compound This example illustrates an embodiment of a ROMP process with activation of the Schiff base substituted ruthenium complex of example 11 shown as complex 70 in FIG. 5 (acting as the catalyst to be activated) by both $HSiCl_3$ and propanol. The procedure of example 17 was repeated with a catalyst/monomer/propanol/silane ratio equal to 1:30,000:90:30, starting from a temperature of 80° C. Reaction was allowed to proceed for 110 seconds until temperature reached a maximum $T_{max}$=218° C., after which time temperature quickly decreases. This shows that, under these experimental conditions, polydicyclopentadiene with a glass transition temperature $T_g$ of about 218° C. can be obtained within about 2 minutes according to the present invention.

EXAMPLE 52

Ring Opening Polymerisation of Dicyclopentadiene with Activation of a Schiff Base Ruthenium Complex with a Silicon Compound The procedure of example 51 was repeated, except that the catalyst/monomer/propanol/silane ratio was changed to 1:20,000:90:30, and that the experiment was started from a temperature of 60° C. Reaction was allowed to proceed for 14 minutes until temperature reached a maximum $T_{max}$=201° C., after which time temperature quickly decreases. This shows, by comparison with example 51, that in the presence of this catalyst polymerisation is slowed down by decreasing the monomer/catalyst ratio and decreasing the starting reaction temperature.

EXAMPLES 53 TO 55

Ring Opening Polymerisation of Dicyclopentadiene with Activation of a Schiff Base Ruthenium Complex with a Silicon Compound The procedure of example 17 was repeated with $CH_3Cl_2SiH$ as an activator, except that 2,6-di-tert-butyl-4-sec-butylphenol was replaced with an alcohol, and that no additive was added in any experiment. The catalyst/monomer/alcohol/silane ratio used was 1:30,000:60:30.

The following table 5 indicates the type of alcohol used in each example, the maximum temperature $T_{max}$ obtained and the time period after which it was achieved.

TABLE 5

| example | alcohol type | time [min.] | $T_{max}$ [° C.] |
|---|---|---|---|
| 53 | 1-propanol | 8.2 | 174 |
| 54 | 2-methyl-1-propanol | 7.9 | 165 |
| 55 | 3-methyl-3buten-1-ol | 9.5 | 182 |

The data presented in table 5 show that it is possible to modulate the glass transition temperature $T_g$ of the polymer obtained while changing the type of further reactant used togather with the silane activator but without significantly changing the time needed for obtaining full polymerisation.

EXAMPLES 56 AND 57

Ring Opening Polymerisation of Dicyclopentadiene with Activation of a Schiff Base Ruthenium Complex with a Titanium Compound The procedure of example 17 was repeated except that $TiCl_4$ was used as an activator, 2,6-di-tert-butyl-4-sec-butylphenol was replaced with an alcohol or another phenol, and no additive was added in any experiment. The catalyst/monomer/alcohol(phenol)/titanium molar ratio used was 1:30,000:90:22.5.

The following table 6 indicates the type of co-reactant used in each example, the maximum temperature $T_{max}$ obtained and the time period after which it was achieved.

TABLE 6

| example | Co-reactant type | time [min.] | $T_{max}$ [° C.] |
|---|---|---|---|
| 56 | 1-propanol | 2.0 | 201 |
| 57 | 3,5-dimethylphenol | 1.1 | 202 |

The data presented in table 6 show that it is possible to keep the advantage of a high glass transition temperature $T_g$ of the polymer obtained while changing the type of activator and while significantly decreasing the time period required for obtaining full polymerisation.

EXAMPLES 58 TO 60

Ring Opening Polymerisation of Dicyclopentadiene with Activation of a Schiff Base Ruthenium Complex with an Aluminium Compound The procedure of example 17 was repeated except that $AlCl_3$ was used as an activator, 2,6-di-tert-butyl-4-sec-butylphenol (ISONOX 132) may be replaced with n-propanol or 3,5-dimethylphenol, and no additive was added in any experiment. The catalyst/monomer/alcohol(phenol)/aluminium molar ratio used was 1:30,000:90:30.

The following table 7 indicates the type of co-reactant used in each example, the maximum temperature $T_{max}$ obtained and the time period after which it was achieved.

TABLE 7

| example | alcohol type | time [min.] | $T_{max}$ [° C.] |
| --- | --- | --- | --- |
| 58 | 1-propanol | 3.3 | 163 |
| 59 | 3,5-dimethylphenol | 1.2 | 170 |
| 60 | ISONOX 132 | 1.0 | 172 |

The data presented in table 7 show that it is possible to modulate the glass transition temperature $T_g$ of the polymer obtained while changing the type of activator and while significantly decreasing the time period required for obtaining full polymerisation.

EXAMPLE 61

Ring Opening Polymerisation of Dicyclopentadiene with Activation of a Schiff Base Ruthenium Complex with a Tin Compound The procedure of example 17 was repeated except that $SnCl_4$ was used as an activator, 2,6-di-tert-butyl-4-sec-butylphenol was replaced with n-propanol, and no additive was added in any experiment. The catalyst/monomer/propanol/tin molar ratio used was 1:30,000:90:22.5. Reaction was allowed to proceed for 171 seconds until temperature reached a maximum $T_{max}$=178° C., after which time temperature quickly decreases. This shows that, under these experimental conditions, polydicyclopentadiene with a glass transition temperature $T_g$ of about 178° C. can be obtained within less than 3 minutes in the presence of a tin-based activating compound.

EXAMPLES 62 TO 64

Ring Opening Polymerisation of Dicyclopentadiene with Activation of a Schiff Base Ruthenium Complex with Silicon Tetrachloride The procedure of example 17 was repeated except that $SiCl_4$ was used as an activator, 2,6-di-tert-butyl-4-sec-butylphenol (ISONOX 132) may be replaced with n-propanol or 3,5-dimethylphenol, and no additive was added in any experiment. The catalyst/monomer/alcohol(phenol)/silicon molar ratio used was 1:30,000:90:22.5.

The following table 8 indicates the type of co-reactant used in each example, the maximum temperature $T_{max}$ obtained and the time period after which it was achieved.

TABLE 8

| example | co-reactant type | time [min.] | $T_{max}$ [° C.] |
| --- | --- | --- | --- |
| 62 | 1-propanol | 4.0 | 184 |
| 63 | 3,5-dimethylphenol | 6.5 | 181 |
| 64 | ISONOX 132 | 6.5 | 184 |

EXAMPLES 65 AND 66

Ring Opening Polymerisation of Dicyclopentadiene with Activation of a Schiff Base Ruthenium Complex with a Silicon Compound The procedure of example 17 was repeated except that $HSiCl_3$ was used as an activator, 2,6-di-tert-butyl-4-sec-butylphenol (ISONOX 132) was replaced with n-propanol or 3,5-dimethylphenol, and no additive was added in any experiment. The catalyst/monomer/alcohol(phenol)/silicon molar ratio used was 1:30,000:90:30.

The following table 9 indicates the type of co-reactant used in each example, the maximum temperature $T_{max}$ obtained and the time period after which it was achieved.

TABLE 9

| example | co-reactant type | time [min.] | $T_{max}$ [° C.] |
| --- | --- | --- | --- |
| 65 | 1-propanol | 5.0 | 185 |
| 66 | 3,5-dimethylphenol | 2.0 | 200 |

EXAMPLE 67

Ring Opening Polymerisation of Dicyclopentadiene with Activation of a Schiff Base Ruthenium Complex with a Phosphorus Compound The procedure of example 17 was repeated except that $PBr_3$ was used as an activator, 2,6-di-tert-butyl-4-sec-butylphenol was replaced with 3,5-dimethylphenol, and no additive was added in this experiment. The catalyst/monomer/phenol/phosphorous molar ratio used was 1:30,000:90:30. Reaction was allowed to proceed for 11.4 minutes until temperature reached a maximum $T_{max}$=156° C., after which time temperature quickly decreases. This shows that, under these experimental conditions, polydicyclopentadiene with a glass transition temperature $T_g$ of about 156° C. can be obtained in the presence of a phosphorous-based activating compound.

EXAMPLES 68 AND 69

Ring Opening Polymerisation of Dicyclopentadiene with Activation of a Schiff Base Ruthenium Complex with a Silicon Compound The procedure of example 17 was repeated except that $H(CH_3)SiCl_2$ was used as an activator, 2,6-di-tert-butyl-4-sec-butylphenol (ISONOX 132) was replaced with a monocarboxylic acid, and no additive was added in any experiment. The catalyst/monomer/acid/silicon molar ratio used was 1:30,000:60:30.

The following table 10 indicates the type of co-reactant used in each example, the maximum temperature $T_{max}$ obtained and the time period after which it was achieved.

TABLE 10

| example | co-reactant type | time [min.] | $T_{max}$ [° C.] |
| --- | --- | --- | --- |
| 68 | Acetic acid | 7.5 | 174 |
| 69 | Benzoic acid | 12.7 | 177 |

All publications and patent applications mentioned in this specification are herein incorporated by reference to the same extent as if each independent publication or patent application was specifically and individually indicated to be incorporated by reference.

What is claimed is:

1. A reaction product, said reaction product being a catalytically active product capable catalyzing the metathesis of an unsaturated compound and formed from reaction of:

(a) a multi-coordinated Schiff-base-substituted monometallic ruthenium metal complex, a salt, or an enantiomer thereof, said monometallic ruthenium metal complex comprising (i) at least one multidentate Schiff base ligand comprising an imino group and being coordinated to the metal, in addition to the nitrogen atom of said imino group, through at least one further heteroatom selected from the group consisting of oxygen, sulfur and selenium, and (ii) at least carbine ligand selected from the group consisting of N-heterocyclic carbine, alkylidene ligands, vinylidene ligands, indenylidene ligands, heteroatom-containing alkylidene ligands and allenylidene ligands, and (iii) at least one anionic ligand wherein said monometallic ruthenium metal complex is free of phosphine ligand; and (b) an activating compound selected from the group consisting of:
zinc compounds represented by the formula $Zn(R_5)_2$ wherein $R_5$ is halogen, $C_{1-7}$ alkyl or aryl,
tin compounds represented by the formula $SnR_9R_{10}R_{11}R_{12}$ wherein each of $R_9$, $R_{10}$, $R_{11}$ and $R_{12}$ is independently selected from the group consisting of halogen, $C_{1-20}$ alkyl, $C_{3-10}$ cycloalkyl, aryl, benzyl and $C_{2-7}$ alkenyl, and
silicon compounds represented by the formula $SiR_{13}R_{14}R_{15}R_{16}$ wherein each of $R_{13}$, $R_{14}$, $R_{15}$ and $R_{16}$ is independently selected from the group consisting of hydrogen, halogen, $C_{1-20}$ alkyl, halo $C_{1-7}$ alkyl, aryl, heteroaryl and vinyl,
wherein the molar ratio of said activating compound to the ruthenium metal of monometallic ruthenium metal complex is from about 5:1 to about 2,000:1, and wherein the reaction product has at least partial cleavage of a bond between said ruthenium and said at least one multidentate Schiff base ligand (i).

2. The product according to claim 1 wherein the number of carbon atoms in said at least one multidentate Schiff base ligand (i), between the nitrogen atom of said imino group and said heteroatom of said at least one multidentate Schiff base ligand (i), is from 2 to 4.

3. The product according to claim 1, wherein said multi-coordinated metal complex further comprises a non-anionic ligand.

4. The product according to any of the claim 1 wherein said at least one multidentate Schiff base ligand (i) has one of the general formulae (IA) and (IB):

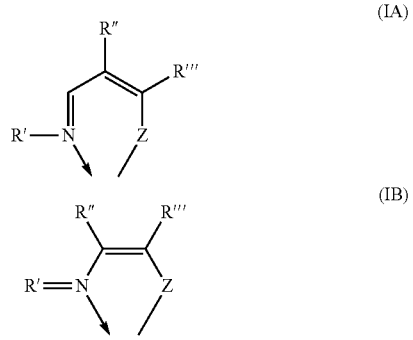

wherein:
Z is selected from the group consisting of oxygen, sulfur and selenium;

R" and R'" are each a radical independently selected from the group consisting of hydrogen, $C_{1-7}$ alkyl, $C_{3-10}$ cycloalkyl, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, aryl and heteroaryl, or R" and R'" together form an aryl or heteroaryl radical, each said radical being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium;

R' is either as defined for R" and R'" when included in a compound having the general formula (IA) or, when included in a compound having the general formula (IB), is selected from the group consisting of $C_{1-7}$ alkylene and $C_{3-10}$ cycloalkylene, the said alkylene or cycloalkylene group being optionally substituted with one or more substituents $R_5$.

5. The product according to claim 1, wherein said multi-coordinated metal complex (a) comprises a ligand that is a derivative having one or more hydrogen atoms substituted with a group providing constraint steric hindrance in a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazolin-2-ylidene), bis(imidazolidin-2-ylidene), pyrrolylidene, pyrazolylidene, dihydropyrrolylidene, pyrrolylidi-nylidene and benzo-fused derivatives thereof, or a non-ionic prophosphatrane superbase.

6. The product according to claim 1, wherein said anionic ligand is selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium, arylammonium, halogen atoms and cyano.

7. The product according to claim 1, wherein said carbene ligand is a phenylindenylidene ligand.

8. The product according to claim 1, wherein said multi-coordinated metal complex further comprises a non-anionic unsaturated ligand $L^1$ selected from the group consisting of aromatic and unsaturated cycloaliphatic groups, the said aromatic or unsaturated cycloaliphatic group being optionally substituted with one or more $C_{1-7}$ alkyl groups or electron-withdrawing groups such as, but not limited to, halogen, nitro, cyano, (thio)carboxylic acid, (thio)carboxylic acid (thio)ester, (thio)carboxylic acid (thio)amide, (thio)carboxylic acid anhydride and (thio)carboxylic acid halide.

9. The product according to claim 1 wherein said multi-coordinated metal complex (a) further comprises a non-anionic ligand $L^2$ selected from the group consisting of $C_{1-7}$ alkyl, $C_{3-10}$ cycloalkyl, arylalkyl and heterocyclic, the said group being optionally substituted with one or more preferably electron-withdrawing substituents such as, but not limited to, halogen, nitro, cyano, (thio)carboxylic acid, (thio)carboxylic acid (thio)ester, (thio)carboxylic acid (thio)amide, (thio)carboxylic acid anhydride and (thio)carboxylic acid halide.

10. The product according to claim 1, wherein the molar ratio of said activating compound to the ruthenium metal of monometallic ruthenium metal complex is from about 15:1 to about 2,000:1.

11. The product according to claim 10, wherein the molar ratio of said activating compound to the ruthenium metal of monometallic ruthenium metal complex is from about 20:1 to about 2,000:1.

12. A method of performing a metathesis reaction of an unsaturated compound in the presence of a catalytic component said method comprising contacting said unsaturated compound with said catalytic component, wherein said catalytic component is the catalytically active reaction product of claim 1.

13. The method according to claim 12, wherein said metathesis reaction is the ring-opening metathesis polymerization of a strained cyclic olefin.

14. The method according to claim 12, wherein said catalytic component is supported on a carrier.

15. The method according to claim 14, wherein said carrier is selected from the group consisting of porous inorganic solids, crystalline molecular sieves, and organic polymer resins.

16. The method according to claim 12, wherein said metathesis reaction is the ring-opening metathesis polymerization of cyclooctadiene or dicyclopentadiene.

17. The method according to claim 12, wherein said metathesis reaction is a ring-closing metathesis reaction.

18. The method according to claim 12, wherein said unsaturated compound is an alkyne or an olefin.

* * * * *